US007767768B2

(12) United States Patent
Chang et al.

(10) Patent No.: US 7,767,768 B2
(45) Date of Patent: Aug. 3, 2010

(54) CROSSLINKED AMINE POLYMERS

(75) Inventors: Han Ting Chang, Livermore, CA (US); Dominique Charmot, Campbell, CA (US); Eric Connor, Los Gatos, CA (US); Florence Roger, Mountain View, CA (US)

(73) Assignee: Ilypsa, Inc., Thousand Oaks, CA (US)

( * ) Notice: Subject to any disclaimer, the term of this patent is extended or adjusted under 35 U.S.C. 154(b) by 199 days.

(21) Appl. No.: 11/577,194

(22) PCT Filed: May 11, 2005

(86) PCT No.: PCT/US2005/016437

§ 371 (c)(1),
(2), (4) Date: Sep. 6, 2007

(87) PCT Pub. No.: WO2006/043984

PCT Pub. Date: Apr. 27, 2006

(65) Prior Publication Data

US 2008/0107737 A1 May 8, 2008

(51) Int. Cl.
*C07C 211/11* (2006.01)
*C08F 26/06* (2006.01)

(52) U.S. Cl. ....................... 525/374; 526/258; 526/310; 424/78.12; 521/36; 524/612; 564/511; 564/512; 525/526

(58) Field of Classification Search ................. 525/374, 525/526, 258, 310; 424/78.12; 521/36; 524/612; 564/511, 512
See application file for complete search history.

(56) References Cited

U.S. PATENT DOCUMENTS

| | | | | |
|---|---|---|---|---|
| 3,308,020 | A | 3/1967 | Wolf et al. | |
| 3,499,960 | A | 3/1970 | Macek et al. | |
| 3,692,895 | A | 9/1972 | Nelson et al. | |
| 3,930,810 | A * | 1/1976 | Gattuso | 44/332 |
| 3,974,272 | A | 8/1976 | Polli et al. | |
| 4,015,939 | A | 4/1977 | Lewin et al. | |
| 4,027,009 | A | 5/1977 | Grier et al. | |
| 4,075,177 | A | 2/1978 | Bonnet et al. | |
| 4,135,880 | A | 1/1979 | Mangiardi et al. | |
| 4,410,688 | A | 10/1983 | Denkewalter et al. | |
| 4,507,466 | A | 3/1985 | Tomalia et al. | |
| 4,558,120 | A | 12/1985 | Tomalia et al. | |
| 4,568,737 | A | 2/1986 | Tomalia et al. | |
| 4,587,329 | A | 5/1986 | Tomalia et al. | |
| 4,599,400 | A | 7/1986 | Tomalia et al. | |
| 4,605,701 | A | 8/1986 | Harada et al. | |
| 4,631,337 | A | 12/1986 | Tomalia et al. | |
| 4,690,985 | A | 9/1987 | Tomalia et al. | |
| 4,734,200 | A | 3/1988 | Berry | |
| 4,737,550 | A | 4/1988 | Tomalia | |
| 4,747,881 | A | 5/1988 | Shaw et al. | |
| 4,902,501 | A | 2/1990 | Bandi et al. | |
| 5,091,175 | A | 2/1992 | Imondi et al. | |
| 5,254,669 | A | 10/1993 | Blackborow | |
| 5,338,532 | A | 8/1994 | Tomalia et al. | |
| 5,380,522 | A | 1/1995 | Day | |
| 5,447,726 | A | 9/1995 | Nomura | |
| 5,451,397 | A | 9/1995 | Albright et al. | |
| 5,487,888 | A | 1/1996 | Mandeville, III et al. | |
| 5,496,545 | A | 3/1996 | Holmes-Farley et al. | |
| 5,530,092 | A | 6/1996 | Meijer et al. | |
| 5,607,669 | A | 3/1997 | Mandeville, III et al. | |
| 5,618,530 | A | 4/1997 | Mandeville, III et al. | |
| 5,667,775 | A | 9/1997 | Holmes-Farley et al. | |
| 5,679,717 | A | 10/1997 | Mandeville, III et al. | |
| 5,693,675 | A | 12/1997 | Mandeville, III et al. | |
| 5,698,662 | A | 12/1997 | Stoelwinder et al. | |
| 5,702,696 | A | 12/1997 | Mandeville, III et al. | |
| 5,833,854 | A | 11/1998 | Zwijnenburg et al. | |
| 5,968,499 | A | 10/1999 | Hider et al. | |
| 5,980,881 | A | 11/1999 | Mitsuka et al. | |
| 5,985,938 | A | 11/1999 | Holmes-Farley et al. | |
| 6,007,803 | A | 12/1999 | Mandeville, III et al. | |
| 6,034,129 | A | 3/2000 | Mandeville, III et al. | |
| 6,060,604 | A | 5/2000 | Yang et al. | |
| 6,129,910 | A | 10/2000 | Holmes-Farley et al. | |
| 6,132,706 | A | 10/2000 | Hider et al. | |
| 6,132,771 | A | 10/2000 | Depui et al. | |

(Continued)

FOREIGN PATENT DOCUMENTS

DE 10305807 A1 8/2004

(Continued)

OTHER PUBLICATIONS

De Brabander-Van Den Berg, E.M.M., et al., "Poly(propylene imine) Dendrimers: Large-Scale Synthesis by Hetereogeneously Catalyzed Hydrogenations," Angew. Chem. Int. Ed. Engl., 1993, pp. 1308-1311, vol. 32, No. 9.

(Continued)

*Primary Examiner*—Robert D. Harlan
(74) *Attorney, Agent, or Firm*—Senniger Powers LLP

(57) ABSTRACT

The present invention provides methods and compositions for the treatment of ion imbalances. In particular, the invention provides polymeric and pharmaceutical compositions comprising crosslinked amine polymers. Methods of use of the polymeric and pharmaceutical compositions for therapeutic and/or prophylactic benefits are disclosed herein. Examples of these methods include the treatment of renal diseases and hyperphosphatemia.

31 Claims, No Drawings

U.S. PATENT DOCUMENTS

| | | | |
|---|---|---|---|
| 6,180,094 B1 | 1/2001 | Sasaki et al. |
| 6,180,754 B1 | 1/2001 | Stutts et al. |
| 6,281,252 B1 | 8/2001 | Holmes-Farley et al. |
| 6,333,051 B1 | 12/2001 | Kabanov et al. |
| 6,361,768 B1 | 3/2002 | Galleguillos et al. |
| 6,362,266 B1 | 3/2002 | Buchholz et al. |
| 6,383,518 B1 | 5/2002 | Matsuda et al. |
| 6,423,754 B1 | 7/2002 | Holmes-Farley et al. |
| 6,471,968 B1 | 10/2002 | Baker, Jr. et al. |
| 6,475,510 B1 | 11/2002 | Venkatesh et al. |
| 6,509,013 B1 | 1/2003 | Holmes-Farley et al. |
| 6,566,407 B2 | 5/2003 | Holmes-Farley et al. |
| 6,593,366 B2 | 7/2003 | Mandeville, III et al. |
| 6,600,011 B2 | 7/2003 | McDonnell et al. |
| 6,638,710 B2 | 10/2003 | Leinenbach et al. |
| 6,646,083 B2 | 11/2003 | Hirano et al. |
| 6,696,087 B2 | 2/2004 | Matsuda et al. |
| 6,726,905 B1 | 4/2004 | Mandeville, III et al. |
| 6,733,780 B1 | 5/2004 | Tyler et al. |
| 6,767,549 B2 | 7/2004 | Mandeville, III et al. |
| 6,844,372 B2 | 1/2005 | Goto et al. |
| 7,067,614 B2 | 6/2006 | Rea |
| 2002/0028887 A1 | 3/2002 | Hirano et al. |
| 2002/0034723 A1 | 3/2002 | Leinenbach et al. |
| 2002/0054903 A1 | 5/2002 | Tyler et al. |
| 2002/0064511 A1 | 5/2002 | Simon et al. |
| 2002/0146386 A1 | 10/2002 | Simon et al. |
| 2002/0168333 A1 | 11/2002 | Burke |
| 2002/0182168 A1 | 12/2002 | Holmes-Farley |
| 2002/0187120 A1 | 12/2002 | Holmes-Farley et al. |
| 2002/0187121 A1 | 12/2002 | Burke |
| 2003/0039627 A1 | 2/2003 | Holmes-Farley et al. |
| 2003/0049226 A1 | 3/2003 | Burke et al. |
| 2003/0078366 A1 | 4/2003 | McDonnell et al. |
| 2003/0091530 A1 | 5/2003 | Goto et al. |
| 2003/0092782 A1 | 5/2003 | Goto et al. |
| 2004/0018169 A1 | 1/2004 | Holmes-Farley et al. |
| 2004/0059065 A1 | 3/2004 | Goto et al. |
| 2004/0120922 A1 | 6/2004 | Burke |
| 2004/0170600 A1 | 9/2004 | Simon et al. |
| 2004/0194334 A1 | 10/2004 | Rea |
| 2005/0096438 A1 | 5/2005 | Chang et al. |
| 2005/0131138 A1 | 6/2005 | Connor et al. |
| 2005/0147580 A1 | 7/2005 | Connor et al. |
| 2005/0165190 A1 | 7/2005 | Chang et al. |
| 2005/0209423 A1 | 9/2005 | Chang et al. |
| 2005/0239901 A1 | 10/2005 | Chang et al. |
| 2005/0276781 A1 | 12/2005 | Ross et al. |

FOREIGN PATENT DOCUMENTS

| | | | |
|---|---|---|---|
| EP | 0373852 | B1 | 10/1994 |
| EP | 0672703 | A1 | 9/1995 |
| EP | 0575596 | B1 | 2/1996 |
| EP | 0707611 | B1 | 9/1997 |
| EP | 0741756 | B1 | 4/1998 |
| EP | 0793960 | B1 | 1/2001 |
| EP | 1153940 | A1 | 11/2001 |
| EP | 1283046 | A1 | 2/2003 |
| EP | 1304104 | A2 | 4/2003 |
| EP | 0997148 | B1 | 7/2003 |
| EP | 1209146 | B1 | 6/2004 |
| JP | 10059851 | A | 3/1998 |
| JP | 10130154 | A | 5/1998 |
| JP | 2003155429 | A | 5/2003 |
| WO | 8200257 | A1 | 2/1982 |
| WO | 9314147 | A1 | 7/1993 |
| WO | 9419379 | A1 | 9/1994 |
| WO | 9427619 | A1 | 12/1994 |
| WO | 9502008 | A1 | 1/1995 |
| WO | 9505184 | A2 | 2/1995 |
| WO | 9519384 | A1 | 7/1995 |
| WO | 9520619 | A1 | 8/1995 |
| WO | 9723514 | A1 | 7/1997 |
| WO | 9749736 | A2 | 12/1997 |
| WO | 9817707 | A1 | 4/1998 |
| WO | 9842355 | A1 | 10/1998 |
| WO | 9914297 | A1 | 3/1999 |
| WO | 9940990 | A1 | 8/1999 |
| WO | 0128527 | A2 | 4/2001 |
| WO | 0138423 | A1 | 5/2001 |
| WO | 0232974 | A2 | 4/2002 |
| WO | 0232974 | A3 | 4/2002 |
| WO | 02077074 | A1 | 10/2002 |
| WO | 2004037274 | A1 | 5/2004 |
| WO | 2005065291 | A2 | 7/2005 |
| WO | 2006040579 | A1 | 4/2006 |

OTHER PUBLICATIONS

Bilicki, C.V., et al., "Effect of Anions on Adsorption of Bile Salts by Colestipol Hydrochloride", Pharmaceutical Research, 1989, pp. 794-797, vol. 6, No. 9, Plenum Publishing Corporation.

Bleyer, A.J., et al., "A Comparison of the Calcium-Free Phosphate Binder Sevelamer Hydrochloride With Calcium Acetate in the Treatment of Hyperphosphatemia in Hemodialysis Patients", American Journal of Kidney Diseases, 1999, pp. 694-701, vol. 33, No. 4, National Kidney Foundation, Inc.

Barsotti et al., "Anion-exchange resins for the uremic hyperphosphatemia," Mineral and Electrolyte Metabolism, 1979, p. 206, vol. 2, No. 1.

Brezina et al., "Acid loading during treatment with sevelamer hydrochloride: mechanisms and clinical implications" Kidney International, 2004, pp. S39-S45, vol. 66.

Buhleier et al., "'Cascade' and 'Nonskid-Chain-Like' Synthesis of Molecular Cavity Topoligies," Synthesis, 1978, pp. 155-158, vol. 02.

Burke, S., "Renagel: reducing serum phosphorus in haemodialysis patients," Hospital Medicine, 2000, pp. 622-627, vol. 61, No. 9.

Burt et al., "In vitro studies using ion exchange resins as potential phosphate binders for renal failure patients," Uremia Investigation, 1985-86, pp. 35-44,vol. 9, No. 1.

Burt et al., "Ion-exchange resins as potential phosphate-binding agents for renal failure patients: Effect of the physicochemical properties of resins on phosphate and bile salt binding," Journal of Pharmaceutical Sciences, 1986, pp. 379-383, vol. 76, No. 5.

Chertow et al., "Long-term effects of sevelalmer hydrochloride on the calcium x phosphate product and lipid profile or haemodialysis patents," Nephrology Dialysis Transplantation, 1999, pp. 2907-2914, vol. 14.

Cholestyramine Package Insert "Cholestyramine for oral suspension," Copley Pharmaceutical, Inc., Canton, MA.

Colestid Package Insert "Colestid micronized colestipol hydrochloride tablets," Pharmacia & Upjohn Company, Kalamazoo, MI.

Coli et al., "Phosphate removal by resin hemoperfusion efficacy and biocompatibility of a new exchange resin," Biomaterials, Artificial Cells, and Immobilization Biotechnology, 1992, pp. 1153-1163, vol. 20, No. 5.

Covassin, L., et al., "Synthesis of Spermidine and Norspermidine Dimers as High Affinity Polyamine Transport Inhibitors, Bioorganic & Medicinal Chemistry Letters," 1999, pp. 1709-1714, vol. 9, Elsevier Science Ltd.

Daniel et al., "Supramolecular H-bonded assemblies of redox-active metallodendrimers and positive and unusual dendritic effects on the recognition of H2PO4," Journal of American Chemical Society, 2003, pp. 1150-1151, vol. 125, No. 5.

De Simone et al., "New microporous cholestyramine analog for treatment of hypercholesterolemia," Journal of Pharmaceutical Sciences, 1978, pp. 1695-1698, vol. 67, No. 12.

Grynpas et al., Organic ion exchange resins as substitutes for aluminum hydroxide gels, Life Support Systems, 1987, pp. 276-278, vol. 4 (Suppl.2).

Hagmaier et al., "Investigation of the efficacy [also "Test of efficacy"] of oxalate-binding anionic exchanger colestid in healthy subjects for use in idiopathic calcium-oxalate-urolithiasis," Helveica Chirurgica. Acta, 1981, pp. 421-424, vol. 48, No. 3/4.
Hardy et al. "Inhibition of gastric secretion by omeprazole and efficiency of calcium carbonate on the control of hyperphosphatemia in patients on chronic hemodialysis," Artificial Organs, 1998, pp. 569-573, vol. 22, No. 7.
Honda et al., "Studies on adsorption characteristics of bile acids and methotrexate to a new type of anion-exchange resin, colestimide," Chemical and Pharmaceutical Bulletin, 2000, pp. 978-981, vol. 48, No. 7.
Hurst et al., "The effect of oral anion exchange resins on FAECAL anions. Comparison with calcium salts and aluminum hydroxide," Clinical Science, 1963, pp. 187-200, vol. 24.
Jansen, Bart A.J., et al., "A Tetranuclear Platinum Compound Designed to Overcome Cisplatin Resistance," Eur. J. Inorg. Chem., 1999, pp. 1429-1433, Wiley-VCH Verlag GmbH, D-69451 Weinheim.
Klapper et al., "Poly(methyleneamine): A polymer with the maximum possible number of amino groups on a polymer backbone," Angew. Chem. Int. Ed., 2003, pp. 4687-4690, vol. 42.
Kioussis et al., "Characterization of anion diffusion in polymer hydrogels used for wastewater remediation," Polymer, 2005, pp. 9342-9347, vol. 46.
Kioussis et al., "Characterization of network morphology in anion binding hydrogels used for wastewater remediation," Polymer, 2005, pp. 10167-10172, vol. 46.
Konechnik et al., "In vitro adsorption of bile salts by colestipol hydrochloride," Pharmaceutical Research, 1989, pp. 619-623, vol. 6, No. 7.
Kurihara et al., "Effect of MCI-196(colestilan) as a phosphate binder on hyperphosphataemia in haemodialysis patients: a double-blind, placebo-controlled, short-term trial," Nephrol Dial Transplant, 2005, pp. 424-430, vol. 20, No. 2.
Malluche, H.H., et al., "Management of hyperphosphataemia of chronic kidney disease: lessons from the past and future directions," Nephrol Dial Transplant, 2002, pp. 1170-1175, vol. 17.
Mazzeo et al., "A phosphate binding assay for sevelamer hydrochloride by ion chromatography," J. Pharm. Biomed. Anal., 1999, pp. 911-915, vol. 19.
McGary et al., "Polycation as an alternative osmotic agent and phosphate binder in peritoneal dialysis," Uremia Investigation, 1984-85, pp. 79-84, vol. 8, No. 2.
Nolan et al., "Endotoxin Binding by Charged and Uncharged Resins," Proceedings of the Society for Experimental Biology and Medicine, 1975, pp. 766-770, vol. 149.
Panova et al., "Interaction of poly(propylenimine) dendrimers with polyanioic hydrogels," Faculty of Chemistry, Moscow State University, 2004, pp. 783-798, vol. 46, No. 5 [with English abstract].
Peppas et al., "Dendrimers and star polymers for pharmaceutical and medical applications," Proceed. Intern. Symp. Control. Rel. Bioact. Mater, 1993, pp. 143-144, vol. 20.
Rauter, H., et al., "Selective Platination of Biologically Relevant Polyamines. Linear Coordinating Spermidine and Spermine as Amplifying Linkers in Dinuclear Platinum Complexes," Inorg. Chem., 1997, pp. 3919-3927, vol. 36, American Chemical Society.
Reiss et al., "Protonation products of pentaamino-pentane as novel building blocks for hydrogen-bonded networks," Acta Crysta., 2000, pp. 284-288, vol. C56.
Ross et al., "Synthesis of molecularly imprinted polymers (MIPs) for phosphate binding," Published in the abstract list of Renal Week Conference (Sep. 20, 2004) ASN.
Schneider et al., "Aluminum-free oral phosphate binder," Dep. Nephrol. Hypertension, 1984, pp. 76-79, vol. 1, No. 2 [Abstract only].
Sechet et al., "Inhibition of gasteric secretion by omeprazole and efficacy of calcium carbonate in the control of hyperphosphatemia in patients on maintenance hemodialysis," Nephrologie, 1999, pp. 213-216, vol. 20, No. 4 [French with English abstract].
Shataeva et al., "Effect on FAF anionite swelling on its sorption properties," Prikl. Biokhim. Microbiol., 1982, pp. 65-70, vol. 18, No. 1 [Russian with English abstract].
Slatopolsky et al., "RenaGel, a nonabsorbed calcium-and aluminum-free phosphate binder, lowers serum phosphorus and parathyroid hormone" Kidney International, 1999, vol. 55, pp. 299-307.
Sugano, M., et al., "A novel use of chitosan as a hypocholesterolemic agent in rats," The American Journal of Clinical Nutrition, 1980, pp. 787-793 vol. 33.
Swearingen et al., "Determination of the binding parameter constants of Renagel capsules and tablets utilizing the Langmuir approximation at various pH by ion chromatography," Journal of Pharmaceutical and Biomedical Analysis, 2002, pp. 195-201, vol. 29.
Tiitu et al., "Aminic epoxy resin hardeners as reactive solvents for conjugated polymers; polyaniline base/epoxy composites for anti-corrosion coatings," Polymer, 2005, pp. 6855-6861, vol. 46.
WelChol Tablets package insert, GelTex Pharmaceuticals, Inc.
Wrong, O.M., "Aluminum Toxicity," Lancet, 1972, pp. 334-335, vol. 2, No. 7772.
Wrong, O.M., "Anion-exchange resins in treatment of uraemic acidosis and hyperphosphataemia," Lancet, 1973, pp. 493, vol. 1, No. 7801.
Zimmer et al., "Complex formation of Ni, Cu, Pd, and Co with 1,2,3,4-tetraaminobutane," Chem. Eur. J., 2001, pp. 917-931, vol. 7, No. 4.
Zimmer et al., "Ligand synthesis and metal complex formation of 1,2,3-triaminopropane," Eur. J. Inorg. Chem., 1998, pp. 2079-2086, vol. 12.

* cited by examiner

CROSSLINKED AMINE POLYMERS

CROSS-REFERENCE

This application is a United States National Stage Application based on International Application No. PCT/US2005/016437.

BACKGROUND OF THE INVENTION

In patients with normal kidney function, calcium and phosphorous balance is maintained through the interaction of parathyroid hormone (PTH) and calcitriol, an active metabolite of vitamin D. PTH provides a mechanism for controlling extracellular calcium and phosphate concentrations by regulating intestinal reabsorption, renal excretion, and exchange of these ions between the extracellular fluid and bone.

With progressive renal insufficiency, however, there is increased phosphorus retention by the failing kidney. In order to restore phosphorus balance, compensatory elevation in PTH levels is triggered, which increases renal resorption of calcium, while decreasing tubular resorption of phosphorus. The net effect of compensatory hyperparathyroidism in this early stage of renal disease is that serum phosphorus levels are maintained within the normal range.

The retention of phosphorus as a result of the decreased ability of the diseased kidney to excrete the filtered phosphate leads to a decrease in serum free calcium, which in turn stimulates the secretion of more PTH. With each progressive reduction in kidney function, a new steady state is achieved in which serum phosphate is restored to normal at the expense of a sustained high level of PTH. The cycle is repeated as renal function declines until sustained and severe hyperparathyroidism is present; eventually the compensatory mechanism is not able to control the increasing serum phosphorous levels. Once the glomerular filtration rate has decreased to <20% of normal, overt hyperphosphatemia becomes evident. In end-stage renal disease patients (where the compensatory mechanism mediated by PTH is no longer effective), the increase in plasma phosphate results not only from decreased excretion but also from continual high levels of PTH, which further exacerbates the problem by releasing calcium and phosphate from the bone.

The clinical manifestations of hyperphosphatemia are varied and have considerable mortality risks. Severe hyperphosphatemia can induce hypocalcemia, which aggravates the imbalance in PTH levels further by increasing the production of this hormone. Hyperphosphatemia inhibits renal synthesis of calcitriol, which causes an exacerbation of the hypocalcemia condition. The occurrence of severe hypocalcemia with tetany and ectopic calcifications is the most severe manifestation of hyperphosphatemia. Calcification may occur in the joints, soft tissues, lungs, kidney, and conjuctiva. Soft tissue calcification has been linked to cardiovascular risk, and cardiovascular disease is the cause of death in more than 45% of all dialysis patients. Renal osteodystrophy with effects on the bones and muscles is common in end stage renal disease (ESRD) patients, as well as severe pruritis. The high PTH level associated with developing and severe renal disease has indirect actions on the central and peripheral nervous system, and the myocardial tissues, creating further disorders such as hyperlipemia, muscle growth retardation, arteriosclerosis, bone loss, and immunodeficiency.

Prevention and treatment of hyperphosphatemia is achieved by a variety of means, including dietary control of phosphorus intake, dialysis and oral phosphate binders. Dialysis, however, does not remove phosphate ions well from the serum because of the slow equilibrium between intracellular and extracellular phosphorus. The treatments of choice focus instead on a phosphorus controlled diet and the administration of phosphate binders taken at meals. A low phosphorus diet is not a long-term option, however, since patient compliance is difficult and the daily dietary phosphorus intake cannot be lowered below ~1000 mg/day, without restricting protein intake even further than the 1.2 g/kg/day of protein recommended for hemodialysis patients.

Oral phosphate binders comprise two main classes: inorganic metal salts and polymer resins, often referred to as metal-free binders. Examples of the former category include compounds such as aluminum carbonate, calcium carbonate, calcium acetate (PhosLo), and lanthanum carbonate (Fosrenol). While aluminum and calcium salts have been the treatment of choice for years, they produce soluble metal ions that cross the gastrointestinal membrane and enter the blood stream, producing toxic effects. For instance, aluminum carbonate salts have been shown to be involved in cases of encephalopathy and aluminum osteopathy due to aluminum bone absorption. Calcium binders also generate large amounts of soluble calcium cations, the absorption of which can cause hypercalcemia. Further, although the causative effect is not fully demonstrated, high calcium x phosphate product has been held responsible for soft tissue calcification and cardiovascular disease. Lanthanum carbonate seems to produce less metal absorption, but bone accumulation of lanthanum has been established and the long-term effect of such accumulation in humans is still unclear.

Metal free binders include ion exchange resins and crosslinked polyallylamine resins. Ion exchange resins include cholestyramine, colestipol hydrochloride, and Dowex. These resins have been proposed as an alternative to metal salts, but their low capacity and their lack of palatability have precluded their wide use in the clinic. Crosslinked polyallylamine, like sevelamer hydrochloride (Renagel), was introduced as the next generation of metal-free phosphate binder resins. However, the phase 1 clinical trials performed on healthy volunteers indicate that the in vivo binding capacity of Renagel is much lower than anticipated from in vitro studies. As a consequence ESRD patients still need a high dosage of Renagel to meet clinical end-points, leading to adverse effect such as gastrointestinal discomfort and problems with patient compliance.

Accordingly, there is a need to develop better phosphate binding therapies, with reduced side effects for patients with hyperphosphatemia.

BRIEF SUMMARY OF THE INVENTION

In one first aspect, the present invention relates to polymers and polymeric compositions comprising crosslinked amine moieties. The polymers can be crosslinked amine polymers. The polymeric compositions can comprise one or more crosslinked amine polymers. Several embodiments of the invention, including this aspect of the invention, are described in further detail as follows. Generally, each of these embodiments can be used in various and specific combination, and in each permutation, with each other aspects and embodiments as described above or below herein.

In a first embodiment the invention is, consists essentially of, or comprises a crosslinked amine polymer comprising an amine of formula I (I)

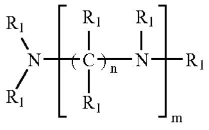

wherein each n, independently, is equal to or greater than 3; m is equal to or greater than 1; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n and each m, independently, is 3 to 20, even more preferably each n and each m, independently, is 3-10. In some embodiments, m is equal to 1 or 2. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

A second embodiment of the invention is, consists essentially of, or comprises a crosslinked amine polymer comprising an amine of formula II (II)

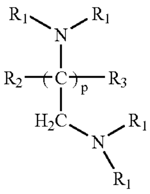

wherein p is 1, 2, 3, or 4; each $R_1$, independently, is H or optionally substituted alkyl or aryl or is linked to a neighboring $R_1$ to form an optionally substituted alicyclic, aromatic, or heterocyclic group; $R_2$ and $R_3$, each independently, are H or optionally substituted alkyl or aryl, with the proviso that when p=1, both $R_2$ and $R_3$ are not H and when p=2, 3, or 4, $R_2$ and $R_3$ are H, alkyl or $—C(R_1)_2—R_4—N(R_1)_2$, $R_4$ being either a bond or methylene; and the amine is crosslinked with a crosslinking agent. In some embodiments, $R_2$ and $R_3$, each independently, can be an amine. Preferably, each $R_1$, independently, is H or optionally substituted lower alkyl. Preferably, each $R_2$ and $R_3$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

A third embodiment of the invention is, consists essentially of, or comprises a crosslinked amine polymer comprising an amine of formula III (III)

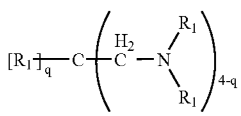

wherein q is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

A fourth embodiment of the invention is, consists essentially of, or comprises a crosslinked amine polymer comprising an amine of formula IV (IV)

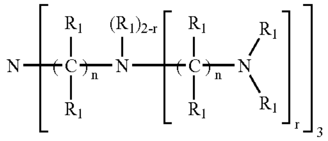

wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 20, even more preferably each n, independently, is 3-10. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Another additional embodiment of the invention is, consists essentially of, or comprises a crosslinked amine polymer, wherein said polymer comprises an amine of formula IV'

(IV)'

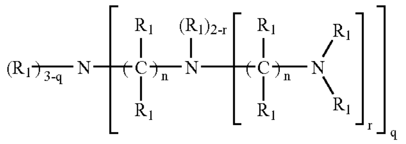

q = 1,2, or 3 wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 20, even more preferably each n, independently, is 3-10. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

A fifth embodiment of the invention is, consists essentially of, or comprises a crosslinked amine polymer comprising an amine of formula V (V)

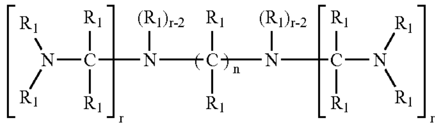

wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Another embodiment of the invention is, consists essentially of, or comprises a crosslinked amine polymer comprising an amine of formula VII (VIII)

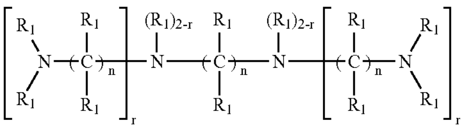

with the proviso that said amine is not a compound of formula V (V)

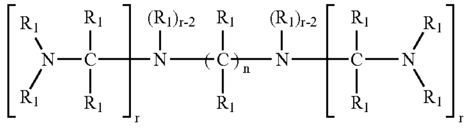

and is not the following amine of formula V'

(V')

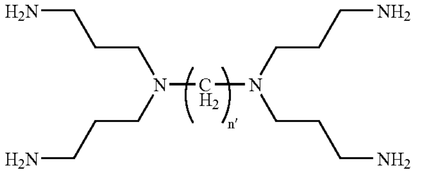

n': 3,4, or 5 wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 10, even more preferably each n, independently, is 6-10. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Another embodiment of the invention is, consists essentially of, or comprises a crosslinked amine polymer comprising an amine of formula VII (VII)

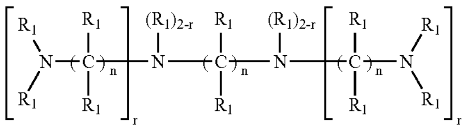

with the proviso that said amine is not a compound of formula V''

(V'')

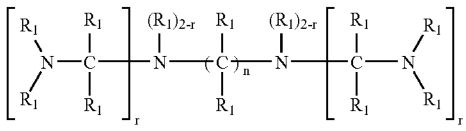

and is not the following amine of formula V'

(V')

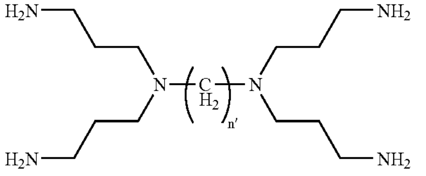

n': 3,4, or 5 wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 10, even more preferably each n, independently, is 6-10. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Another embodiment of the invention is, consists essentially of, or comprises a crosslinked amine polymer comprising an amine of formula VII (VII)

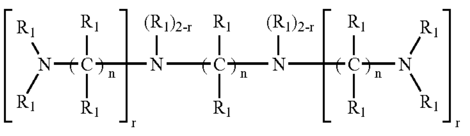

with the proviso that said amine is not a compound of formula V (V)

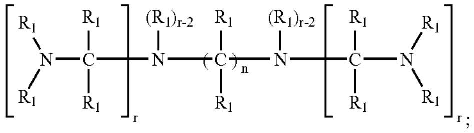

is not a compound of formula V"

(V")

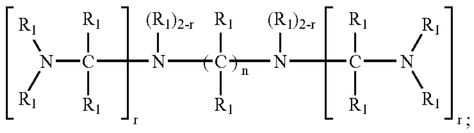

and is not the following amine of formula V'

(V')

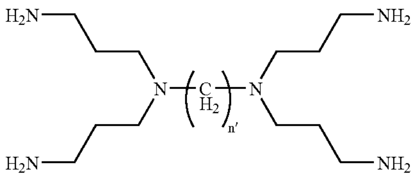

n': 3,4, or 5 wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 10, even more preferably each n, independently, is 6-10. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Another embodiment of the invention is a crosslinked amine polymer comprising an amine of formula VII (VII)

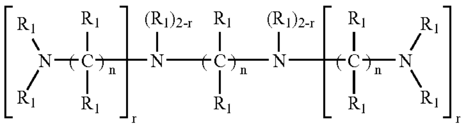

with the proviso that said amine is not an amine of formula V'

(V')

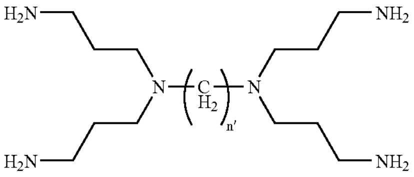

n': 3,4, or 5 wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 10, even more preferably each n, independently, is 6-10. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

A preferred embodiment of the invention is, consists essentially of, or comprises a crosslinked amine polymer comprising the following amine of formula VIII (VIII)

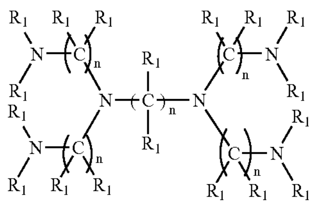

with the proviso that said amine is not an amine of formula V'

(V')

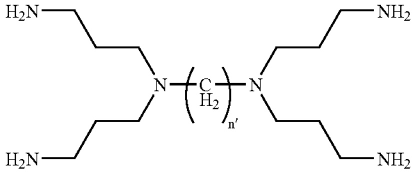

n': 3,4, or 5 wherein each n, independently, is equal to or greater than 3 and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 10, even more preferably each n, independently, is 6-10. The different "n" in the formula can be the same; different "n" in the formula can be different; or some of the "n" in the formula can be the same and the others can be different. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Another preferred embodiment of the invention is, consists essentially of, or comprises a crosslinked amine polymer comprising the following amine of formula IX (IX)

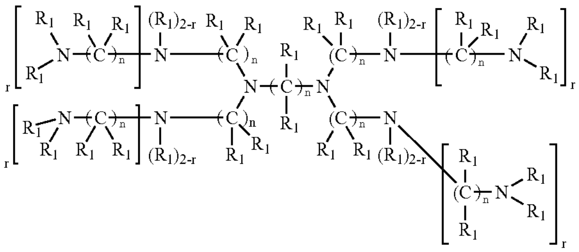

r = 0, 1, 2 with the proviso that said amine is not an amine of formula V'

(V')

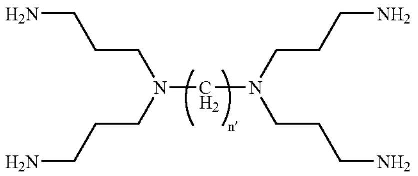

n': 3,4, or 5 wherein each n, independently, is equal to or greater than 3 and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 10, even more preferably each n, independently, is 6-10. The different "n" in the formula can be the same; different "n" in the formula can be different; or some of the "n" in the formula can be the same and the others can be different. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Another preferred embodiment of the invention is, consists essentially of, or comprises a crosslinked amine polymer comprising the following amine of formula X (X)

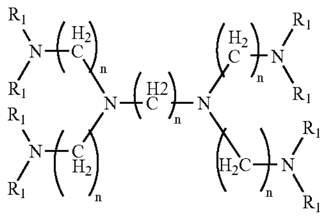

with the proviso that said amine is not an amine of formula V'

(V')

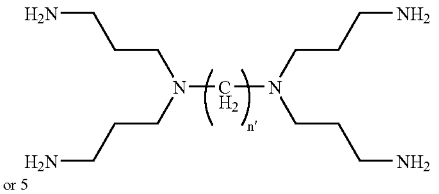

n': 3,4, or 5 wherein each n, independently, is equal to or greater than 3 and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 10, even more preferably each n, independently, is 6-10. The different "n" in the formula can be the same; different "n" in the formula can be different; or some of the "n" in the formula can be the same and the others can be different. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Another embodiment of the invention is, consists essentially of or comprises a crosslinked amine polymer comprising the following amine of formula V'''

(V)'

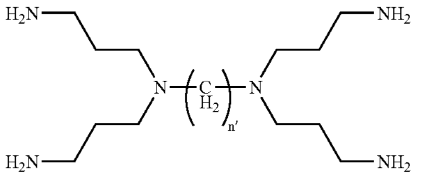

wherein n' is equal to greater than 6 and the amine is crosslinked with a crosslinking agent. Preferably n' is 6-20, even more preferred is n' equal to 6-10, and most preferred is n' equal to 6-8. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

In another second aspect, the invention provides methods of treating (e.g., a condition of) an animal, including a human. The method generally involves administering an effective amount of a polymer or a polymeric composition described herein, such as a crosslinked amine polymer or a composition consisting essentially of, or comprising a crosslinked amine polymer, in each case as described herein. Each of the embodiments of the invention can be used in various and specific combination, and in each permutation, with this aspect of the invention. Also, this aspect of the invention can be combined with each of the other aspects and embodiments described above or below herein.

In a third aspect, the invention relates to methods comprising use of a polymer or a polymeric composition or a pharmaceutical composition described herein, such as a crosslinked amine polymer or a composition consisting essentially of, or comprising a crosslinked amine polymer, in each case as described herein, for manufacture of a medicament for use as a pharmaceutical for treating a condition of an animal, including a human. Each of the embodiments of the invention can be used in various and specific combination, and in each permutation, with this aspect of the invention. Also, this aspect of the invention can be combined with each of the other aspects and embodiments described above or below herein.

Another fourth aspect of the invention is a pharmaceutical composition comprising one or more polymers, such as a crosslinked amine polymer, of the present invention with at least one pharmaceutically acceptable carrier. The polymers and/or polymeric compositions described herein have several therapeutic applications, and such therapeutic applications are considered in connection with each aspect of this invention, including the first, second, third or fourth aspects of this invention. For example, the polymers of the invention such as crosslinked amine polymers (as well as compositions comprising the same) are useful in removing phosphate, from the gastrointestinal tract. Accordingly, the polymers of the invention such as crosslinked amine polymers (as well as compositions comprising the same) can be useful for treating conditions such as hyperphosphatemia. In some embodiments, the crosslinked amine polymers are used in the treatment of (e.g., conditions involving or resulting from) phosphate imbalance disorders and renal diseases. Each of the embodiments of the invention can be used in various and specific combination, and in each permutation, with this aspect of the invention. Also, this aspect of the invention can be combined with each of the other aspects and embodiments described above or below herein.

In yet another fifth aspect of the invention, the crosslinked amine polymers or compositions comprising such polymers are useful for removing other anionic solutes, such as chloride, bicarbonate, and/or oxalate ions. Hence, in one approach, this aspect of the invention can be directed to methods for removing anionic solutes, especially for removing anionic solutes such as chloride, bicarbonate, and/or oxalate ions. Polymers removing oxalate ions find use in the treatment of oxalate imbalance disorders. Polymers removing chloride ions find use in treating acidosis, for example. In some embodiments, the crosslinked amine polymers are useful for removing bile acids and related compounds.

The invention further provides, in another sixth aspect, compositions containing an anion-binding polymer, such as a phosphate-binding polymer, and preferably such as any of the above polymers or any other polymer described herein, including cross-linked amine polymers, where the polymer is in the form of particles and where the polymeric particles are encased in an outer shell. Each of the embodiments of the invention can be used in various and specific combination, and in each permutation, with this aspect of the invention. Also, this aspect of the invention can be combined with each of the other aspects and embodiments described above or below herein.

In another seventh aspect, the invention provides pharmaceutical compositions. In one embodiment of this aspect of the invention, the pharmaceutical composition contains an anion-binding polymer, such as a phosphate-binding polymer, and preferably such as a polymer of the invention as described herein, including cross-linked amine polymers, and a pharmaceutically acceptable excipient. In some additional embodiments of this aspect of the invention, the pharmaceutical composition is a liquid formulation in which the polymer is dispersed in a liquid vehicle of water and suitable excipients. In some alternative embodiments of this aspect of the invention, the invention provides a pharmaceutical composition comprising an anion-binding polymer that binds a target anion, preferably a phosphate-binding polymer, and one or more suitable pharmaceutical excipients, where the composition is in the form of a chewable or mouth-disintegrating tablet. In some embodiments within this embodiment the chewable tablet can contain one or more pharmaceutical excipients selected from the group consisting of sucrose, mannitol, xylitol, maltodextrin, fructose, sorbitol, and combinations thereof. In some embodiments within this embodiment, the chewable tablet can be produced by a process where the polymer is pre-formulated with the excipient to form a solid solution. In some embodiments the target anion of the polymer is phosphate. In some embodiments the anion-binding polymer is more than about 50% of the weight of the tablet. In some embodiments, the tablet is of cylindrical shape with a diameter of about 22 mm and a height of about 4 mm and the anion binding polymer comprises more than about 1.6 gm of the total weight of the tablet. In some of the chewable tablets of the invention, the excipients are chosen from the group consisting of sweetening agents, binders, lubricants, and disintegrants. Optionally, the polymer is present as particles of less than about 40 μm mean diameter. In some of these embodiments, the sweetening agent is selected from the group consisting of sucrose, mannitol, xylitol, maltodextrin, fructose, and sorbitol, and combinations thereof. In some further alternative embodiments of this aspect of the invention, the invention provides a pharmaceutical composition comprising an anion-binding polymer that binds a target anion, preferably a phosphate-binding polymer, and one or more suitable pharmaceutical excipients, where the composition does not result in, or essentially does not result in, or minimizes the extent of, undesirable side effects, optionally swelling-related side effects, for example after being administered to an animal subject such as a human. In yet some additional embodiments of this aspect of the invention, the invention provides a pharmaceutical composition comprising an anion-binding polymer that binds a target anion, preferably a phosphate-binding polymer, and one or more suitable pharmaceutical excipients, where the composition does not result in, or essentially does not result in, or minimizes the extent of one or more of constipation, dyspepsia, bloating and combinations thereof, for example after being administered to an animal subject such as a human. Each of the embodiments of the invention can be used in various and specific combination, and in each permutation, with this aspect of the invention. Also, this aspect of the invention can be combined with each of the other aspects and embodiments described above or below herein.

DETAILED DESCRIPTION OF THE INVENTION

Crosslinked Amine Polymers

In one aspect, the present invention provides methods of using compositions comprising a polymer that contains crosslinked amine moieties. Polymers, including homopolymers and copolymers, with repeating crosslinked amine units are referred to herein as crosslinked amine polymers. The repeating amine units in the polymer can be separated by the same or varying lengths of repeating linker (or intervening) units. In some embodiments, the polymers comprise of repeat units of an amine plus intervening linker unit. In other embodiments, multiple amine units are separated by one or more linker units.

In a first embodiment the invention is a method for removing phosphate from the gastrointestinal tract of an animal by administering an effective amount of a crosslinked amine polymer, wherein said polymer comprises an amine of formula I (I)

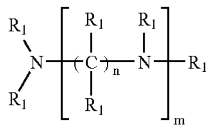

wherein each n, independently, is equal to or greater than 3; m is equal to or greater than 1; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n and each m, independently, is 3 to 20, even more preferably each n and each m, independently, is 3-10. In some embodiments, m is equal to 1 or 2. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Preferred amines of the invention include:

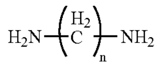

n: 3,4, or 5

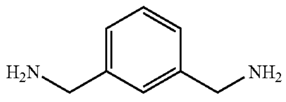 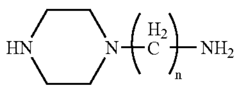

Preferably n is 3-20, more preferably n is 3 to 15, and most preferably n is 3-8.

A second embodiment of the invention is a method of removing phosphate from the gastrointestinal tract of an animal subject by administering an effective amount of a crosslinked amine polymer, wherein said polymer comprises an amine of formula II (II)

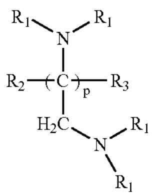

wherein p is 1, 2, 3, or 4; each $R_1$, independently, is H or optionally substituted alkyl or aryl or is linked to a neighboring $R_1$ to form an optionally substituted alicyclic, aromatic, or heterocyclic group; $R_2$ and $R_3$, each independently, are H or optionally substituted alkyl or aryl, with the proviso that when p=1, both $R_2$ and $R_3$ are not H and when p=2, 3, or 4, $R_2$ and $R_3$ are H, alkyl or $—C(R_1)_2—R_4—N(R_1)_2$, $R_4$ being either a bond or methylene; and the amine is crosslinked with a crosslinking agent. In some embodiments, $R_2$ and $R_3$, each independently, can be an amine. Preferably, each $R_1$, independently, is H or optionally substituted lower alkyl. Preferably, each $R_2$ and $R_3$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Preferred amines of the invention include:

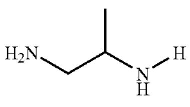 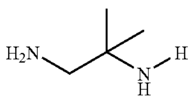

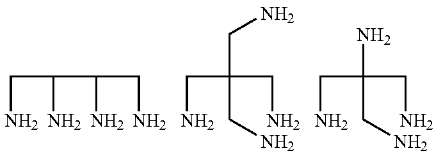

A third embodiment of the invention is a method of removing phosphate from the gastrointestinal tract of an animal by administering an effective amount of a crosslinked amine polymer, wherein said polymer comprises an amine of formula III (III)

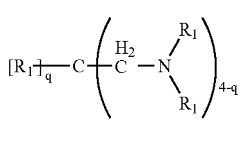

wherein q is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Preferred amines of the invention include:

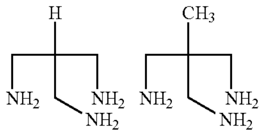

A fourth embodiment of the invention is a method of removing phosphate from the gastrointestinal tract of an animal by administering an effective amount of a crosslinked amine polymer, wherein said polymer comprises an amine of formula IV (IV)

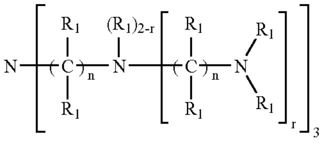

wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 20, even more preferably each n, independently, is 3-10. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Another embodiment of the invention is a method of removing phosphate from the gastrointestinal tract of an animal by administering an effective amount of a crosslinked amine polymer, wherein said polymer comprises an amine of formula IV'

(IV)'

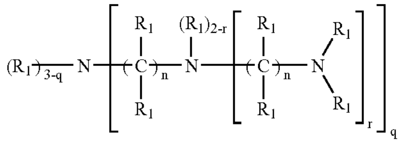

q = 1,2, or 3 wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 20, even more preferably each n, independently, is 3-10. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

A preferred amine of the invention includes:

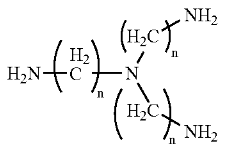

Preferably, each n, independently, is 3 to 20, even more preferably each n, independently, is 3-10.

A fifth embodiment of the invention is a method of removing phosphate from the gastrointestinal tract of an animal by administering an effective amount of a crosslinked amine polymer, wherein said polymer comprises an amine of formula V (V)

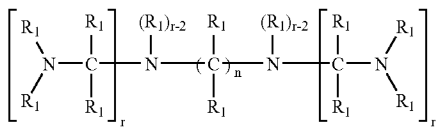

wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Preferred amines of the invention include:

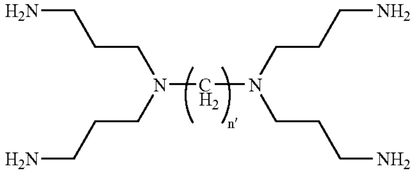

n': 3,4, or 5

Another embodiment of the invention is a method of removing phosphate from the gastrointestinal tract of an animal by administering an effective amount of a crosslinked amine polymer comprising an amine of formula VII (VII)

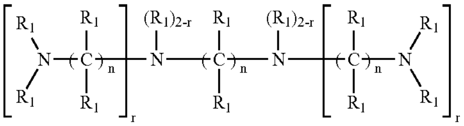

with the proviso that said amine is not a compound of formula V (V)

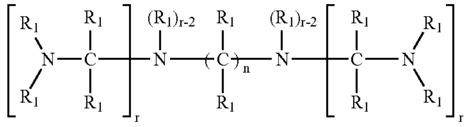

and is not the following amine of formula V'

(V')

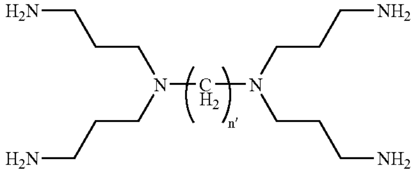

n': 3,4, or 5 wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 10, even more preferably each n, independently, is 6-10. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Yet another embodiment of the invention is a method of removing phosphate from the gastrointestinal tract of an animal by administering an effective amount of a crosslinked amine polymer comprising an amine of formula VII (VII)

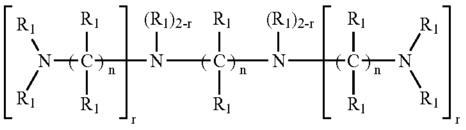

with the proviso that said amine is not a compound of formula V"

(V")

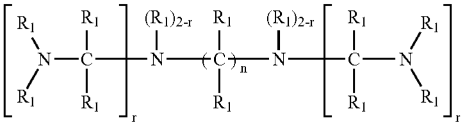

and is not the following amine of formula V'

(V')

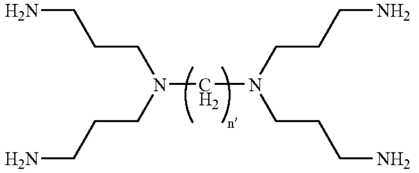

n': 3,4, or 5 wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 10, even more preferably each n, independently, is 6-10. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Another embodiment of the invention is a method of removing phosphate from the gastrointestinal tract of an animal by administering an effective amount of a crosslinked amine polymer comprising an amine of formula VII (VII)

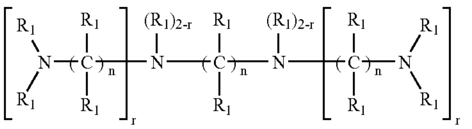

with the proviso that said amine is not a compound of formula V (V)

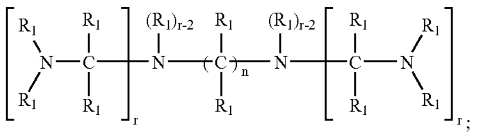

is not a compound of formula V"

(V'')

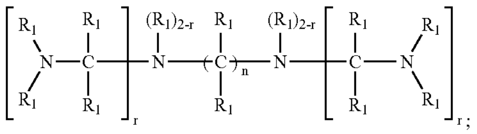

and is not the following amine of formula V'

(V')

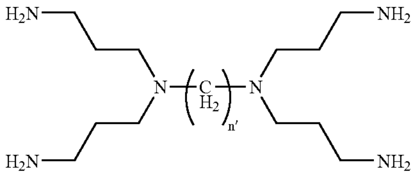

n': 3,4, or 5 wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 10, even more preferably each n, independently, is 6-10. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

One embodiment of the invention is a method of removing phosphate from the gastrointestinal tract of an animal by administering an effective amount of a crosslinked amine polymer comprising an amine of formula VII (VII)

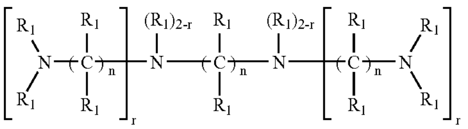

with proviso that said amine is not an amine of formula V'

(V')

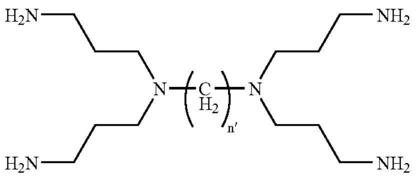

n': 3,4, or 5 wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 10, even more preferably each n, independently, is 6-10. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Another method of the invention is a method of removing phosphate from the gastrointestinal tract of an animal by administering an effective amount of a crosslinked amine polymer comprising the following amine of formula VIII (VIII)

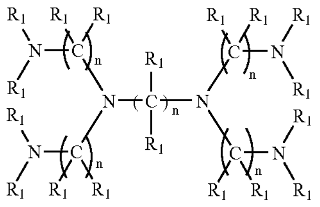

with proviso that said amine is not an amine of formula V'

(V')

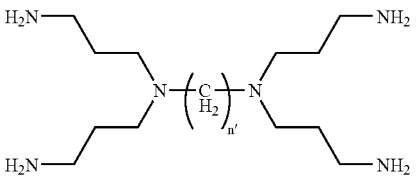

n': 3,4, or 5 wherein each n, independently, is equal to or greater than 3 and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 10, even more preferably each n, independently, is 6-10. The different "n" in the formula can be the same; different "n" in the formula can be different; or some of the "n" in the formula can be the same and the others can be different. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Another method of the invention is a method of removing phosphate from the gastrointestinal tract of an animal by administering an effective amount of a crosslinked amine polymer comprising the following amine of formula IX (IX)

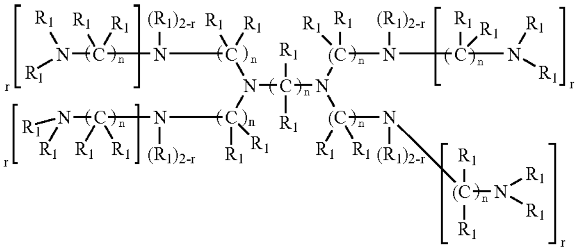

r = 0, 1, 2 with the proviso that said amine is not an amine of formula V'

(V')

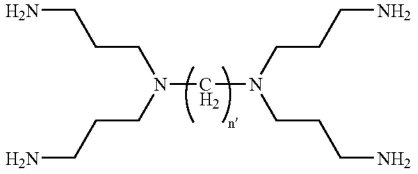

n': 3,4, or 5 wherein each n, independently, is equal to or greater than 3 and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 10, even more preferably each n, independently, is 6-10. The different "n" in the formula can be the same; different "n" in the formula can be different; or some of the "n" in the formula can be the same and the others can be different. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

Yet another method of the invention is a method of removing phosphate from the gastrointestinal tract of an animal by administering an effective amount of a crosslinked amine polymer comprising the following amine of formula X (X)

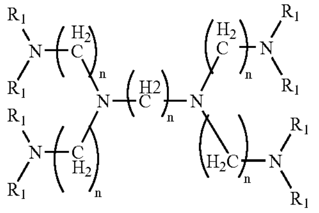

with proviso that said amine is not an amine of formula V'

(V')

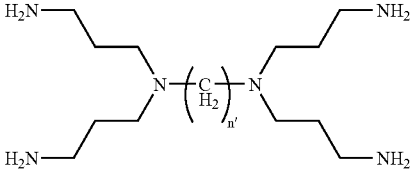

n': 3,4, or 5 wherein each n, independently, is equal to or greater than 3 and each $R_1$, independently, is H or optionally substituted alkyl or aryl or is linked to a neighboring $R_1$ to form an optionally substituted alicyclic, aromatic, or heterocyclic group; and the amine is crosslinked with a crosslinking agent. Preferably, each n, independently, is 3 to 10, even more preferably each n, independently, is 6-10. The different "n" in the formula can be the same; different "n" in the formula can be different; or some of the "n" in the formula can be the same and the others can be different. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

A preferred method of the invention is a method of removing phosphate from the gastrointestinal tract of an animal by administering an effective amount of a crosslinked amine polymer comprising the following amine of formula V'''

(V''')

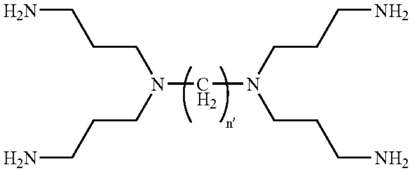

wherein n' is equal to greater than 6 and the amine is crosslinked with a crosslinking agent. Preferably n' is 6-20, even more preferred is n' equal to 6-10, and most preferred is n' equal to 6-8. Preferred crosslinking agents are 1,3-dichloropropane or epichlorohydrin. Preferred crosslinker to amine molar ratios comprise between about 0.2 to about 10, more preferably about 0.5 to about 5, and most preferably about 0.5 to about 2.

In another aspect, the present invention provides compositions comprising a polymer that contains crosslinked amine moieties. These polymers, including homopolymers and copolymers, comprise of repeating crosslinked amine units.

In a first embodiment the invention is a crosslinked amine polymer, wherein said polymer comprises an amine of formula I as described above. A second embodiment of the invention is a crosslinked amine polymer, wherein said polymer comprises an amine of formula II as described above. A third embodiment of the invention is a crosslinked amine polymer, wherein said polymer comprises an amine of formula III as described above. A fourth embodiment of the invention is a crosslinked amine polymer, wherein said polymer comprises an amine of formula IV as described above. A fifth embodiment of the invention is a crosslinked amine polymer, wherein said polymer comprises an amine of formula V as described above.

The polymers comprising of an amine of Formula II have been described above with p=1-4. In addition, in some of the embodiments, the amines of Formula II include amines wherein p is greater than 4. In various embodiments, p can be more than 8, more than 12, more than 16, or more than 20. In other embodiments, p can be less than 25, less than 20, less than 15, or less than 10. In the formulas described herein, preferably, each n, independently, is 3 to 50, even more preferably each n, independently, is 6-20; and most preferably each n, independently, is 3-10. It is also intended that in some embodiments, each n across the formula is different; the different n's across the formula can be the same; and some of the n's across the formula are the same. Preferably, each $R_1$, independently, is H or optionally substituted lower alkyl. Preferred optionally substituted lower alkyls include unsubstituted $C_{2-6}$ alkyl and amine substituted $C_{2-6}$ alkyl. Preferably, each m, independently, is 1 to 20; even more preferably each m, independently, is 2-15; and most preferably each m, independently, is 5 to 10. Preferably, each $R_2$ and $R_3$, independently, is H or optionally substituted lower alkyl. Preferred optionally substituted lower alkyls include unsubstituted $C_{2-6}$ alkyl and amine substituted $C_{2-6}$ alkyl.

The amines represented by general formulas I-VI can be synthesized by methods well known in the art. These synthesis techniques include catalytic conversion from alcohols, reductive amination of carbonyl compounds, Michael additions, and hydrogenation of nitrites (see, for example, Karsten Eller et al, Ullmann's Encyclopedia of Industrial Chemistry 2002 by Wiley-VCH Verlag GmbH & Co. KGaA). Several small amine monomers and/or amine plus intervening linker units are also commercially available.

In one embodiment, an amine useful in the present invention, tetramethylene tetramine, depicted below, is synthesized by catalytic hydrogenation of the commercially available diaminomaleonitrile (DAMN):

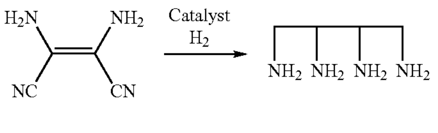

Polymerization can be achieved by methods known to those in the art, examples of which are illustrated in detail in the Examples disclosed herein. For example, the crosslinking reaction is carried out either in solution of bulk (i.e. using the neat amine and neat crosslinker compounds) or in dispersed media. When a bulk process is used, solvents are selected so that they co-dissolve the reactants and do not interfere with the amine crosslinking reaction. Suitable solvents include water, low boiling alcohols (methanol, ethanol, butanol), dimethylformamide, dimethylsulfoxide, acetone, methylethylketone, and the like.

Processes in dispersed media, include inverse suspension, direct suspension and aerosols, and the like. The continuous phase can be selected from apolar solvents such as toluene, benzene, hydrocarbon, halogenated solvents, supercritical carbon dioxide, and the like. With a direct suspension process, water can be used, although salt brines are also useful to "salt out" the amine and crosslinker reagents in a droplet separate phase, as described in U.S. Pat. No. 5,414,068.

The crosslinker to amine mole ratios control the extent of gel material formed as well as its crosslinking density. Too low a ratio may lead to incomplete crosslinking and formation of soluble oligomers, while too high a ratio may produce extremely tight network with little binding properties. The amine component can be either one or a combination of several amines, and the same applies to the crosslinker component. Optimization may be required for any new combination of amines and crosslinkers, since the functionality of either can influence the extent of gel formation and swelling characteristics. In some embodiments, crosslinker to amine molar ratios comprise between about 0.2 to about 10, preferably about 0.5 to about 5, and most preferably about 0.5 to about 2.

The crosslinking reaction is run in a batch or semi continuous mode. In the latter mode, either the amine or the crosslinker is added as the initial charge and the co-reactant is then metered up for a given period of time. In one embodiment, a soluble prepolymer is first prepared by adding the entire amine monomer component and then adding continuously a fraction of the crosslinker, forming a syrup. The syrup is then emulsified as droplets in an oil continuous phase and the remaining fraction of crosslinker is added to form crosslinked beads. When the crosslinker is an alkylhalide compound, a base can be used to scavenge the acid formed during the reaction. Inorganic or organic bases are suitable. NaOH is preferred. The base to crosslinker ratio is preferably between about 0.5 to about 2.

Polymers of the invention are crosslinked materials, meaning that they do not dissolve in solvents, and, at most, swell in solvents. The rate of swelling is expressed as the weight ratio of the swollen gel in a buffer to the dried crosslinked polymer. The rate of swelling in physiological isotonic buffer, representative of the milieu of use, i.e. the gastrointestinal tract, is typically in the range of about 1.2 to about 100, preferably about 2 to 20.

The polymers described herein exhibit phosphate binding properties. Phosphate binding capacity is a measure of the amount of phosphate ion a phosphate binder can bind in a given solution. For example, binding capacities of phosphate binders can be measured in vitro, e.g., in water or in saline solution, or in vivo, e.g., from phosphate urinary excretion, or ex vivo, for example using aspirate liquids, e.g., chyme obtained from lab animals, patients or volunteers. Measurements can be made in a solution containing only phosphate ion, or at least no other competing solutes that compete with phosphate ions for binding to the polymer resin. In these cases, a non interfering buffer would be used. Alternatively, measurements can be made in the presence of other competing solutes, e.g., other ions or metabolites, that compete with phosphate ions (the target solute) for binding to the resin.

Phosphate binding capacity for a polymer can be calculated as $V^*(C_{start}-C_{eq})/P$, expressed in mmol/gr, where V is the fixed volume of the solution used, in L; $C_{start}$ is the initial phosphate ion concentration of the solution in mM; $C_{eq}$ is the equilibrium phosphate ion concentration in the solution in mM, after a weight P, in grams, of polymer is added and equilibration allowed.

The phosphate binding capacity can range from about 0.5 mmol/gr to about 10 mmol/gr, preferably from about 2.5 mmol/gr to about 8 mmol/gr, and even more preferably from about 3 mmol/gr to about 6 mmol/gr. Several techniques are known in the art to determine the phosphate binding capacity. Examples of suitable techniques are described in the Examples section below.

Amines that may be used in the present invention are not limited to, but are typically small amines that serve as monomers or parts of monomeric units for the polymerization reactions. Examples of amines that are suitable for synthesis of the polymers of the present invention include, but are not limited to, the amines shown in Table 1.

TABLE 1

| Label | Type | Structure | MW (g/mol) |
|---|---|---|---|
| B-SM-20-TeA | Tetramine | 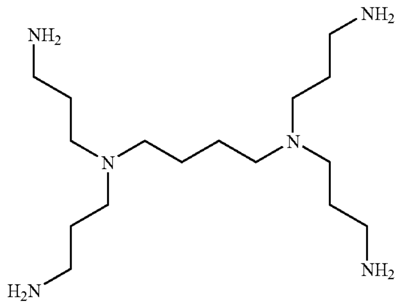 | 316.54 |
| B-SM-22-DA | Diamine | 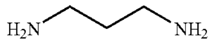 | 61.1 |
| B-SM-23-DA | Diamine | 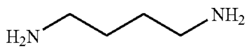 | 88.15 |
| B-SM-24-DA | Diamine | 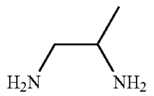 | 74.13 |
| B-SM-25-DA | Diamine | 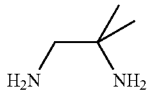 | 88.15 |
| B-SM-26-DA | Diamine | 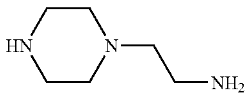 | 129.21 |
| B-SM-27-DA | Diamine | 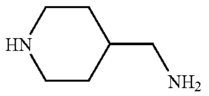 | 114.19 |
| B-SM-28-TA | Triamine | 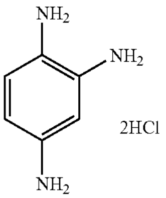 | 196.08 |
| B-SM-29-TA | Triamine | 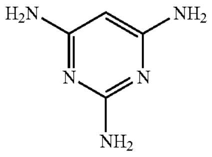 | 125.13 |

TABLE 1-continued

| Label | Type | Structure | MW (g/mol) |
|---|---|---|---|
| B-SM-31-DA | Diamine | 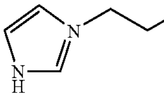 2HCl | 184.07 |
| B-SM-32-DA | Diamine | 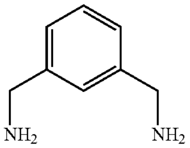 | 136.2 |

Crosslinking agents are typically compounds having at least two functional groups that are selected from a halogen group, carbonyl group, epoxy group, ester group, acid anhydride group, achid halide group, isocyanate group, vinyl group, and chloroformate group. The crosslinking agent may be attached to the carbon backbone or to the pendant nitrogen of the amine polymer. Examples of crosslinked that are suitable for synthesis of the polymers of the present invention include, but are not limited to, the crosslinkers shown in Table 2.

TABLE 2

| Label | Structure | Mw |
|---|---|---|
| X-EP-1 | 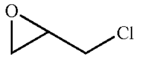 | 92.52 |
| X-EP-2 | 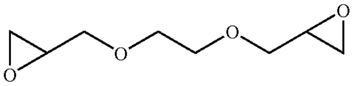 | 174.19 |
| X-EP-3 | 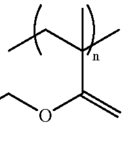 | |
| X-EP-4 | 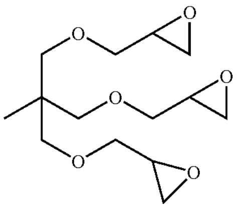 | 302.37 |
| X-EP-5 | 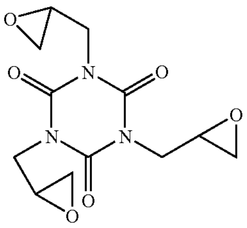 | 297.27 |

TABLE 2-continued

| Label | Structure | Mw |
|---|---|---|
| X-EP-6 | 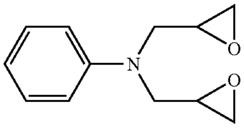 | 277.32 |
| X-EP-7 | 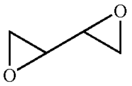 | 86.09 |
| X-EP-8 | 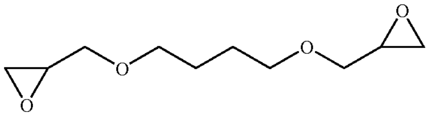 | 202.25 |
| X-Cl-1 | 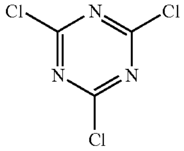 | 184.41 |
| X-Cl-2 | 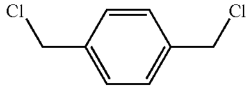 | 175.06 |
| X-Cl-3 | 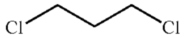 | 112.99 |
| X-Cl-4 | 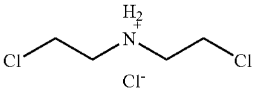 | 178.49 |
| X-Cl-5 | 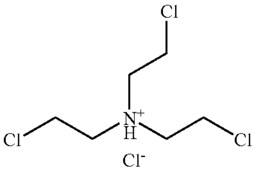 | 240.99 |
| X-Cl-6 | 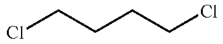 | 127.01 |

TABLE 2-continued
| Label | Structure | Mw |
|---|---|---|
| X-AC-1 | 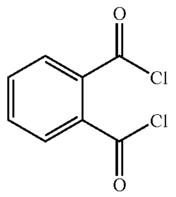 | 203.02 |
| X-AC-2 | 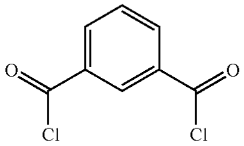 | 203.02 |
| X-AC-3 | 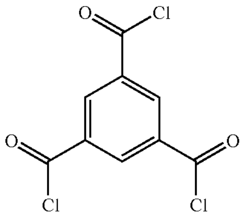 | 265.48 |
| X-AC-4 | 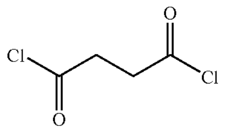 | 154.98 |
| X-AH-1 | 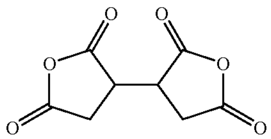 | 198.13 |
| X-AH-2 | 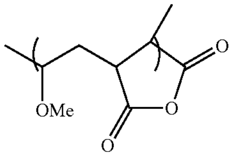 | |
| X-AH-3 | 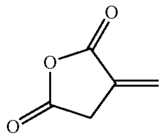 | 112.08 |
| X-Mc-1 | 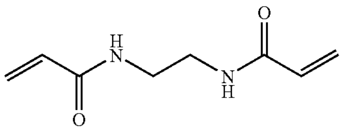 | 168.2 |
| X-Mc-2 | 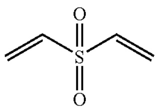 | 118.16 |
TABLE 2-continued
| Label | Structure | Mw |
|---|---|---|
| X-Mc-3 | 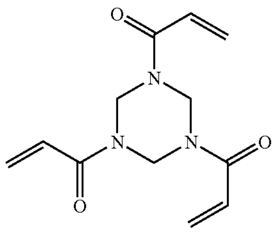 | 249.27 |
| X-Mc-4 | | 158.15 |
| X-IC-1 | 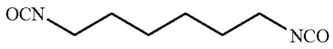 | 168.19 |
| X-IC-2 | 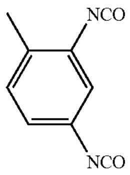 | 174.16 |
| X-IC-3 | 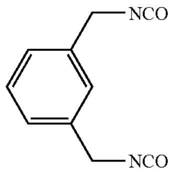 | 188.18 |
| X-IC-4 | 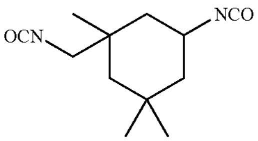 | 222.28 |
| X-ME-1 | 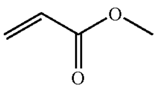 | 86.09 |
| X-ME-2 | 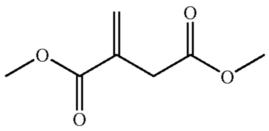 | 158.16 |
| X-ME-3 | 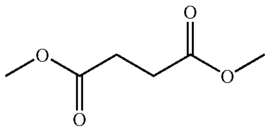 | 146.14 |
| X-ME-4 | 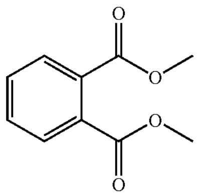 | 194.19 |

TABLE 2-continued

| Label | Structure | Mw |
|---|---|---|
| X-ME-5 | 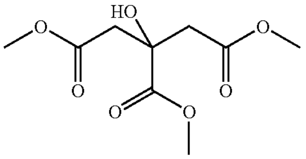 | 234.2 |
| X-ME-6 | 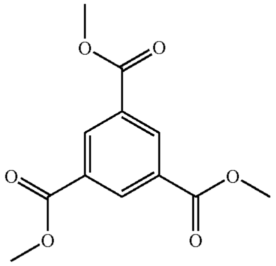 | 252.22 |
| X-ME-7 | 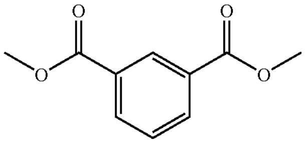 | 194.19 |
| X-ME-8 | 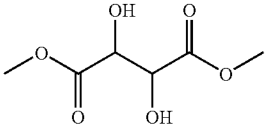 | 178.14 |
| X-ME-9 | 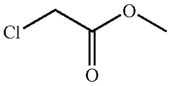 | 108.53 |

Other aspects of the invention are a crosslinked amine polymer comprising an amine of formula VI

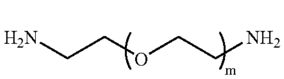

(VI)

and methods of using the same; wherein each m, independently, is equal to or greater than 3 and the amine is crosslinked with a crosslinking agent.

Core-Shell Compositions

One aspect of the invention is core-shell compositions comprising a polymeric core and shell. In some embodiments, the polymeric core comprises of the crosslinked polymers described herein. The shell material can be chemically anchored to the core material or physically coated. In the former case, the shell can be grown on the core component through chemical means, for example by: chemical grafting of shell polymer to the core using living polymerization from active sites anchored onto the core polymer; interfacial reaction, i.e., a chemical reaction located at the core particle surface, such as interfacial polycondensation; and using block copolymers as suspending agents during the core particle synthesis.

The interfacial reaction and use of block polymers are preferred techniques when chemical methods are used. In the interfacial reaction pathway, typically, the periphery of the core particle is chemically modified by reacting small molecules or macromolecules on the core interface. For example, an amine containing ion-binding core particle is reacted with a polymer containing amine reactive groups such as epoxy, isocyanate, activated esters, halide groups to form a crosslinked shell around the core.

In another embodiment, the shell is first prepared using interfacial polycondensation or solvent coacervation to produce capsules. The interior of the capsule is then filled up with core-forming precursors to build the core within the shell capsule.

In some embodiments, using the block copolymer approach, an amphiphilic block copolymer can be used as a suspending agent to form the core particle in an inverse or direct suspension particle forming process. When an inverse water-in-oil suspension process is used, then the block copolymer comprises a first block soluble in the continuous oil phase and another hydrophilic block contains functional groups that can react with the core polymer. When added to the aqueous phase, along with core-forming precursor, and the oil phase, the block copolymer locates to the water-in-oil interface and acts as a suspending agent. The hydrophilic block reacts with the core material, or co-reacts with the core-forming precursors. After the particles are isolated from the oil phase, the block copolymers form a thin shell covalently attached to the core surface. The chemical nature and length of the blocks can be varied to vary the permeation characteristics of the shell towards solutes of interest.

When the shell material is physically adsorbed on the core material, well known techniques of microencapsulation such as solvent coacervation, fluidized bed spray coater, or multi-emulsion processes can be used. A preferred method of microencapsulation is the fluidized bed spray coater in the Wurster configuration. In yet another embodiment, the shell material is only acting temporarily by delaying the swelling of the core particle while in the mouth and esophagus, and optionally disintegrates in the stomach or duodenum. The shell is then selected in order to hinder the transport of water into the core particle, by creating a layer of high hydrophobicity and very low liquid water permeability.

In one embodiment the shell material is preferentially carrying negative charges while being in the milieu of use. Not being limited to one mechanism of action, it has been observed that negatively charged shell material coated on anion-binding beads enhance the binding of small inorganic ions with a low charge density (such as phosphate) over competing ions with greater valency or size. For example, it has been observed that crosslinked amine polymer core particles coated with a polyanionic shell have a higher binding capacity of phosphate ions as measured in synthetic GI environment. Competing anions such as citrate, bile acids and fatty acids among others, have a lesser relative affinity to the anion binding core possibly as a result of their limited permeability across the shell.

Preferred shell materials are polymers carrying negative charges in the pH range typically found in the intestine. Examples include, but are not limited to, polymers that have pendant acid groups such as carboxylic, sulfonic, hydrosulfonic, sulfamic, phosphoric, hydrophosphoric, phosphonic, hydrophosphonic, phosphoramidic, phenolic, boronic and a combination thereof. The polymer can be protonated or unprotonated; in the latter case the acidic anion can be neutralized with pharmaceutically acceptable cations such as Na, K, Li, Ca, Mg, and $NH_4$.

In another embodiment the polyanion can administered as a precursor that ultimately activates as a polyanion: for instance certain labile ester or anhydride forms of either polysulfonic or polycarboxylic acids are prone to hydrolysis in the acidic environment of the stomach and can convert to the active anions.

The shell polymers can be either linear, branched, hyperbranched, segmented (i.e. backbone polymer arranged in sequence of contiguous blocks of which at least one contains pendant acidic groups), comb-shaped, star-shaped or crosslinked in a network, fully and semi-interpenetrated network (IPN). The shell polymers are either random or blocky in composition and either covalently or physically attached to the core material. Examples of such acidic shell polymers include, but are not limited to poly(acrylic acid), poly(styrene sulfonate), carboxymethyl cellulose, cellulose acetate phthalate, hydroxypropyl methylcellulose phthalate, carrageenan, alginate, or poly(methacrylic acid) esters, acrylic/maleic acid copolymers, styrene/maleic acid polymers, itaconic acid/acrylic copolymers, and fumaric/acrylic acid copolymers.

In some preferred embodiments the shell polymers are selected amongst pharmaceutically acceptable polymers such as Eudragit L100-55 and Eudragit L100 (methacrylic acid esters, Degussa/Roehm), Carbopol 934 (polyacrylic acid, Noveon), C-A-P NF (cellulose acetate phthalate—Eastman), Eastacryl (methacrylic acid esters—Eastman), Carrageenan and Alginate (FMC Biopolymer), Anycoat-P (Samsung Fine Chemicals—HPMC Phthalate), or Aqualon (carboxymethyl cellulose—Hercules), methylvinylether/maleic acid copolymers (Gantrez), and styrene/maleic acid (SMA).

The shell can be coated by a variety of methods. In one embodiment, the shell materials are added in the drug formulation step as an active excipient; for example, the shell material can be included in a solid formulation as a powder, which is physically blended with the phosphate-binding polymer and other excipients, optionally granulated, and compressed to form a tablet. Thus, in some embodiments, the shell material need not cover the core material in the drug product. For example, it has been found advantageous to add the acidic shell polymer together with the anion binding core polymer formulated in the shape of a tablet, capsule, gel, liquid, etc, wafer, extrudates and the shell polymer can then dissolve and distribute itself uniformly as a shell coating around the core while the drug product equilibrates in the mouth, esophagus or ultimately in the site of action, i.e. the GI tract. Not intending to be bound to one theory, it is hypothesized that the positively charged anion binding material has a strong affinity to the polyanionic shell material and thus tends to spontaneously form a core-shell structure by charge neutralization.

In some embodiments, the shell is a thin layer of shell polymer. The layer can be a molecular layer of polyanion on the core particle surface. The weight to core ratio can be between about 0.0001% to about 30%, preferably comprised between about 0.1% to about 5%

Preferably the shell polymers low minimum in molecular weight such that they do not freely permeate within the core pore volume nor elute from the core surface. Preferably the molecular weight of the shell acidic polymer Mw is about 1000 g/mole, more preferably about 5000 g/mole, and even more preferably about 20,000 g/mole The anionic charge density of the shell material (as prevailing in the milieu of use) is typically comprised between 0.5 mEq/gr to 22 mEq/gr, preferably 2 mEq/gr to 15 mEq/gr. If a coating process is used to form the shell on the polymer particles as part of the manufacture of the dosage form, then procedures known from those skilled-in-the-art in the pharmaceutical industry are applicable. In a preferred embodiment, the shell is formed in a fluidized bed coater (Wurster coater). In an alternate embodiment, the shell is formed through controlled precipitation or coascervation, wherein the polymer particles are suspended in a polymer solution, and the solvent properties are changed in such a way as to induce the polymer to precipitate onto or coat the polymer particles.

Suitable coating processes include the procedures typically used in the pharmaceutical industry. Typically, selection of the coating method is dictated by a number of parameters, that include, but are not limited to the form of the shell material (bulk, solution, emulsion, suspension, melt) as well as the shape and nature of the core material (spherical beads, irregular shaped, etc.), and the amount of shell deposited.

Treatment of Phosphate Imbalance Disorders and Renal Diseases

The term "phosphate imbalance disorder" as used herein refers to conditions in which the level of phosphorus present in the body is abnormal. One example of a phosphate imbalance disorder includes hyperphosphatemia. The term "hyperphosphatemia" as used herein refers to a condition in which the element phosphorus is present in the body at an elevated level. Typically, a patient is often diagnosed with hyperphosphatemia if the blood phosphate level is, for example, above about 4.5 milligrams per deciliter of blood and/or glomerular filtration rate is reduced to, for example, more than about 20%.

Other diseases that can be treated with the methods, compositions, and kits of the present invention include hypocalcemia, hyperparathyroidism, depressed renal synthesis of calcitriol, tetany due to hypocalcemia, renal insufficiency, and ectopic calcification in soft tissues including calcifications in joints, lungs, kidney, conjuctiva, and myocardial tissues. Also, the present invention can be used to treat ESRD and dialysis patients, including prophylactic treatment of any of the above.

Also, the polymers described herein can be used as an adjunct to other therapies e.g. those employing dietary control of phosphorus intake, dialysis inorganic metal salts and/or other polymer resins.

The compositions of the present invention are also useful in removing chloride, bicarbonate, iron ions, oxalate, and bile acids from the gastrointestinal tract. Polymers removing oxalate ions find use in the treatment of oxalate imbalance disorders, such as such as oxalosis or hyperoxaluria that increases the risk of kidney stone formation. Polymers removing chloride ions find use in treating acidosis, heartburn, acid reflux disease, sour stomach or gastritis, for example. In some embodiments, the compositions of the present invention are useful for removing fatty acids, bilirubin, and related compounds. Some embodiments may also bind and remove high molecular weight molecules like proteins, nucleic acids, vitamins or cell debris.

The present invention provides methods, pharmaceutical compositions, and kits for the treatment of animal. The term "animal" or "animal subject" as used herein includes humans as well as other mammals. One embodiment of the invention is a method of removing phosphate from the gastrointestinal tract of an animal by administering an effective amount of at least one of the crosslinked amine polymers described herein.

The term "treating" and its grammatical equivalents as used herein includes achieving a therapeutic benefit and/or a prophylactic benefit. By therapeutic benefit is meant eradication, amelioration, or prevention of the underlying disorder being treated. For example, in a hyperphosphatemia patient, therapeutic benefit includes eradication or amelioration of the underlying hyperphosphatemia. Also, a therapeutic benefit is achieved with the eradication, amelioration, or prevention of one or more of the physiological symptoms associated with the underlying disorder such that an improvement is observed in the patient, notwithstanding that the patient may still be afflicted with the underlying disorder. For example, administration of crosslinked amine polymers, described herein, to a patient suffering from renal insufficiency and/or hyperphosphatemia provides therapeutic benefit not only when the patient's serum phosphate level is decreased, but also when an improvement is observed in the patient with respect to other disorders that accompany renal failure and/or hyperphosphatemia like ectopic calcification and renal osteodistrophy. For prophylactic benefit, for example, the crosslinked amine polymers may be administered to a patient at risk of developing hyperphosphatemia or to a patient reporting one or more of the physiological symptoms of hyperphosphatemia, even though a diagnosis of hyperphosphatemia may not have been made.

The pharmaceutical compositions of the present invention include compositions wherein the crosslinked amine polymers are present in an effective amount, i.e., in an amount effective to achieve therapeutic and/or prophylactic benefit. The actual amount effective for a particular application will depend on the patient (e.g. age, weight) the condition being treated; and the route of administration. Determination of an effective amount is well within the capabilities of those skilled in the art, especially in light of the disclosure herein.

The effective amount for use in humans can be determined from animal models. For example, a dose for humans can be formulated to achieve circulating and/or gastrointestinal concentrations that have been found to be effective in animals.

The dosages of the crosslinked amine polymers in animals will depend on the disease being, treated, the route of administration, and the physical characteristics of the animal being treated. In some embodiments, the dosage levels of the crosslinked amine polymers for therapeutic and/or prophylactic uses can be from about 1 gm/day to about 30 gm/day. It is preferred that these polymers are administered along with meals. The polymers may be administered one time a day, two times a day, or three times a day. The preferred dosage range is from about 2 gm/day to about 20 gm/day and an even preferred dosage range is from about 3 gm/day to about 7 gm/day. The dose of the polymers described herein can be less than about 50 gm/day, preferably less than about 40 gm/day, more preferably less than about gm/day, even more preferably less than about 30 gm/day, even more preferred less than about 20 gm/day, and most preferred is less than about 10 gm/day.

Preferably, the crosslinked amine polymers used for therapeutic and/or prophylactic benefits can be administered alone or in the form of a pharmaceutical composition. The pharmaceutical compositions comprise the crosslinked amine polymers, one or more pharmaceutically acceptable carriers, diluents or excipients, and optionally additional therapeutic agents. For example, the crosslinked amine polymers of the present invention may be co-administered with other active pharmaceutical agents depending on the condition being treated. Examples of pharmaceutical agents that maybe co-administered include, but are not limited to, proton pump inhibitors, calcimimetics (for example, cinacalcet), Vitamin D and analogs thereof, and phosphate binders. Examples of suitable phosphate binders include, but are not limited to, aluminum carbonate, calcium carbonate, calcium acetate (PhosLo), lanthanum carbonate (Fosrenol), and Renagel. This co-administration can include simultaneous administration of the two agents in the same dosage form, simultaneous administration in separate dosage forms, and separate administration. For example, for the treatment of hyperphosphatemia, the crosslinked amine polymers may be co-administered with calcium salts which are used to treat hypoclacemia resulting from hyperphosphatemia. The calcium salt and the polymer can be formulated together in the same dosage form and administered simultaneously. Alternatively, the calcium salt and the polymer can be simultaneously administered, wherein both the agent are presenting separate formulation. In another alternative, the calcium salt can be administered just followed by the polymer, or vice versa. In the separate administration protocol, the polymer and calcium slat may be administered a few minutes apart, or a few hours apart, or a few days apart.

The polymer can be administered by injection, topically, orally, transdermally, or rectally. Preferably, the polymer or the pharmaceutical composition comprising the polymer is administered orally. The oral form in which the polymer is administered can include powder, tablet, capsule, solution, or emulsion. The effective amount can be administered in a single dose or in a series of doses separated by appropriate time intervals, such as hours.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Suitable techniques for preparing pharmaceutical compositions of the amines are well known in the art.

In some embodiments the polymers of the invention are provided as pharmaceutical compositions in the form of chewable tablets. In addition to the active ingredient, the following types of excipients are commonly used: a sweetening agent to provide the necessary palatability, plus a binder where the former is inadequate in providing sufficient tablet hardness; a lubricant to minimize frictional effects at the die wall and facilitate tablet ejection; and, in some formulations a small amount of a disintegrant is added to facilitate mastication. In general excipient levels in currently-available chewable tablets are on the order of 3-5 fold of active ingredient(s) whereas sweetening agents make up the bulk of the inactive ingredients.

The present invention provides chewable tablets that contain a polymer or polymers of the invention and one or more pharmaceutical excipients suitable for formulation of a chewable tablet. The polymer used in chewable tablets of the invention preferably has a swelling ratio while transiting the oral cavity and in the esophagus of less than about 5, preferably less than about 4, more preferably less than about 3, more preferably less than 2.5, and most preferably less than about 2. In some embodiments the polymer is an anion-binding polymer such as a phosphate- or oxalate binding polymer; in a preferred embodiment, the polymer is a phosphate-binding polymer. The tablet comprising the polymer, combined with suitable excipients, provides acceptable organoleptic properties such as mouthfeel, taste, and tooth packing, and at the same time does not pose a risk to obstruct the esophagus after chewing and contact with saliva.

In some aspects of the invention, the polymer(s) provide mechanical and thermal properties that are usually performed by excipients, thus decreasing the amount of such excipients required for the formulation. In some embodiments the active ingredient (e.g., polymer, preferably an anion-binding polymer) constitutes over about 30%, more preferably over about 40%, even more preferably over about 50%, and most preferably more than about 60% by weight of the chewable tablet, the remainder comprising suitable excipient(s). In some embodiments the polymer, e.g., an anion-binding polymer, comprises about 0.6 gm to about 2.0 gm of the total weight of the tablet, preferably about 0.8 gm to about 1.6 gm. In some embodiments the polymer, e.g., an anion-binding polymer, comprises more than about 0.8 gm of the tablet, preferably more than about 1.2 gm of the tablet, and most preferably more than about 1.6 gm of the tablet. The polymer is produced to have appropriate strength/friability and particle size to provide the same qualities for which excipients are often used, e.g., proper hardness, good mouth feel, compressibility, and the like. Particle size for polymers used in chewable tablets of the invention is less than about 80, 70, 60, 50, 40, 30, or 20 microns mean diameter. In preferred embodiments, the particle size is less than about 80, more preferably less than about 60, and most preferably less than about 40 microns.

Pharmaceutical excipients useful in the chewable tablets of the invention include a binder, such as microcrystalline cellulose, colloidal silica and combinations thereof (Prosolv 90), carbopol, providone and xanthan gum; a flavoring agent, such as sucrose, mannitol, xylitol, maltodextrin, fructose, or sorbitol; a lubricant, such as magnesium stearate, stearic acid, sodium stearyl fumurate and vegetable based fatty acids; and, optionally, a disintegrant, such as croscarmellose sodium, gellan gum, low-substituted hydroxypropyl ether of cellulose, sodium starch glycolate. Other additives may include plasticizers, pigments, talc, and the like. Such additives and other suitable ingredients are well-known in the art; see, e.g., Gennaro A R (ed), *Remington's Pharmaceutical Sciences,* 20th Edition.

In some embodiments the invention provides a pharmaceutical composition formulated as a chewable tablet, comprising a polymer described herein and a suitable excipient. In some embodiments the invention provides a pharmaceutical composition formulated as a chewable tablet, comprising a polymer described herein, a filler, and a lubricant. In some embodiments the invention provides a pharmaceutical composition formulated as a chewable tablet, comprising a polymer described herein, a filler, and a lubricant, wherein the filler is chosen from the group consisting of sucrose, mannitol, xylitol, maltodextrin, fructose, and sorbitol, and wherein the lubricant is a magnesium fatty acid salt, such as magnesium stearate.

The tablet may be of any size and shape compatible with chewability and mouth disintegration, preferably of a cylindrical shape, with a diameter of about 10 mm to about 40 mm and a height of about 2 mm to about 10 mm, most preferably a diameter of about 22 mm and a height of about 6 mm.

In one embodiment, the polymer is pre-formulated with a high Tg/high melting point low molecular weight excipient such as mannitol, sorbose, sucrose in order to form a solid solution wherein the polymer and the excipient are intimately mixed. Method of mixing such as extrusion, spray-drying, chill drying, lyophilization, or wet granulation are useful. Indication of the level of mixing is given by known physical methods such as differential scanning calorimetry or dynamic mechanical analysis.

Methods of making chewable tablets containing pharmaceutical ingredients, including polymers, are known in the art. See, e.g., European Patent Application No. EP373852A2 and U.S. Pat. No. 6,475,510, and Remington's Pharmaceutical Sciences, which are hereby incorporated by reference in their entirety.

In some embodiments the polymers of the invention are provided as pharmaceutical compositions in the form of liquid formulations. In some embodiments the pharmaceutical composition contains an ion-binding polymer dispersed in a suitable liquid excipient. Suitable liquid excipients are known in the art; see, e.g., *Remington's Pharmaceutical Sciences.*

All publications and patent applications mentioned in this specification are herein incorporated by reference to the same extent as if each individual publication or patent application was specifically and individually indicated to be incorporated by reference.

It will be apparent to one of ordinary skill in the art that many changes and modification can be made to the disclosures presented herein without departing from the spirit or scope of the appended claims.

EXAMPLES

Example 1

Libraries of Crosslinked Polymers Formed in a Bulk Solution Process and Measurement for Phosphate Binding Capacity Creation of Polymer Libraries The following five examples each comprise a library comprising up to 24 crosslinked polymers. Polymers were prepared in batch reactors arranged in a 4×6 array format. Each reactor had either a 350 microliters or a 3 ml volume, was magnetically stirred, and temperature-controlled. In a typical procedure, amine, crosslinkers, solvents and optionally base were dispensed robotically in each reactor, optionally under agitation. The reactors were then sealed and heated up to the indicated temperature for 15 hours. The reactor array was then dismounted and plugs of crosslinked polymers transferred in glass vials, ground, washed repeatedly with deionized water, and lyophilized. The five libraries are identified below in Table 3 along with the corresponding reaction conditions used in their creation.

TABLE 3

| Example | Library identification | Reaction temperature (° C.) | Reactor volume (microliters) |
|---|---|---|---|
| 1 | 100275 | 85 | 350 |
| 2 | 100277 | 60 | 350 |
| 3 | 100279 | 80 | 350 |
| 4 | 100353 | 80 | 350 |
| 5 | 100384 | 80 | 3000 |

Phosphate Binding Capacity Measurements in a Non Interfering Buffer

Binding capacities for phosphate ion were also determined for each of the polymers of the libraries. An aliquot of dried resin of weight P(gr), was mixed under gentle agitation with a fixed volume, V(L), of a phosphate ion solution of concentration $C_{start}$(mM) buffered at pH 6.5. The solution can be referred to as a non-interfering buffer as it contains no other competing solutes that compete with the phosphate ions for binding to the polymer resin. After resin equilibration, the solution was decanted by centrifugation and the supernatant analyzed for residual phosphate concentration by ionic chromatography, $C_{eq}$(mM). The binding capacity was calculated as $V*(C_{start}-C_{eq})/P$, expressed in mmol/gr as indicated in the tables for the corresponding polymers.

Results

Tables 4-8 provide materials and the quantities used in forming the polymers of each of the 5 libraries, along with the measured phosphate binding capacities in a non interfering buffer for the polymers formed. Entries correspond to the weight of chemicals used in each reaction well in mg, along with the phosphate binding capacity of the polymer gel obtained (blank indicates no crosslinked gel was formed in that particular reaction).

TABLE 4

Library: Plate3 (ID: 100275) Unit: mg

| Row | Col | water | B-SM-22-DA | X—Cl-3 | NaOH | DMSO | Phosphate binding (mmol/gr) |
|---|---|---|---|---|---|---|---|
| 1 | 1 | 128.51 | 67.74 | 51.63 | 9.14 | 0.00 | |
| 1 | 2 | 130.70 | 57.94 | 61.82 | 10.94 | 0.00 | |
| 1 | 3 | 132.33 | 50.61 | 69.43 | 12.29 | 0.00 | |
| 1 | 4 | 133.59 | 44.93 | 75.33 | 13.33 | 0.00 | 3.042 |
| 1 | 5 | 134.60 | 40.39 | 80.04 | 14.17 | 0.00 | 0 |
| 1 | 6 | 135.43 | 36.69 | 83.89 | 14.85 | 0.00 | 0 |
| 2 | 1 | 136.42 | 32.26 | 88.50 | 15.66 | 0.00 | 3.703 |
| 2 | 2 | 137.05 | 29.41 | 91.45 | 16.19 | 0.00 | 3.624 |
| 2 | 3 | 137.58 | 27.03 | 93.93 | 16.63 | 0.00 | 2.858 |
| 2 | 4 | 138.03 | 25.00 | 96.03 | 17.00 | 0.00 | 2.566 |
| 2 | 5 | 138.42 | 23.26 | 97.84 | 17.32 | 0.00 | 2.761 |
| 2 | 6 | 138.76 | 21.74 | 99.42 | 17.60 | 0.00 | 2.82 |
| 3 | 1 | 132.04 | 64.98 | 49.52 | 17.53 | 34.60 | |
| 3 | 2 | 134.77 | 55.13 | 58.82 | 20.82 | 47.26 | |
| 3 | 3 | 136.79 | 47.87 | 65.67 | 23.25 | 57.22 | |
| 3 | 4 | 138.34 | 42.30 | 70.93 | 25.11 | 65.27 | 3.087 |
| 3 | 5 | 139.57 | 37.90 | 75.09 | 26.58 | 71.91 | 2.946 |
| 3 | 6 | 140.56 | 34.32 | 78.47 | 27.78 | 77.48 | 2.535 |
| 4 | 1 | 141.75 | 30.06 | 82.48 | 29.20 | 79.73 | 2.674 |
| 4 | 2 | 142.50 | 27.35 | 85.04 | 30.11 | 90.45 | 3.038 |
| 4 | 3 | 143.13 | 25.09 | 87.18 | 30.86 | 97.98 | 2.895 |
| 4 | 4 | 143.66 | 23.17 | 88.99 | 31.50 | 103.56 | 2.571 |
| 4 | 5 | 144.12 | 21.52 | 90.54 | 32.05 | 107.86 | 2.636 |
| 4 | 6 | 0.00 | 0.00 | 0.00 | 0.00 | 0.00 | 5.374 |

TABLE 5

Library: Plate1 (ID: 100277) Unit: mg

| Row | Col | water | B-SM-20-TeA | X-EP-1 | X-EP-4 | DMF | Phosphate binding (mmol/gr) |
|---|---|---|---|---|---|---|---|
| 1 | 1 | 123.69 | 110.75 | 12.95 | 0.00 | | |
| 1 | 2 | 124.02 | 107.66 | 16.36 | 0.00 | 0.00 | |
| 1 | 3 | 124.33 | 104.74 | 19.59 | 0.00 | 0.00 | |
| 1 | 4 | 124.63 | 101.98 | 22.65 | 0.00 | 0.00 | |
| 1 | 5 | 124.91 | 99.35 | 25.55 | 0.00 | 0.00 | 4.183 |
| 1 | 6 | 125.17 | 96.86 | 28.31 | 0.00 | 0.00 | 4.237 |
| 2 | 1 | 125.59 | 92.98 | 32.61 | 0.00 | 0.00 | 4.631 |
| 2 | 2 | 125.89 | 90.08 | 35.81 | 0.00 | 0.00 | 4.594 |
| 2 | 3 | 126.18 | 87.37 | 38.81 | 0.00 | 0.00 | 4.667 |
| 2 | 4 | 126.45 | 84.81 | 41.64 | 0.00 | 0.00 | 4.586 |
| 2 | 5 | 126.71 | 82.40 | 44.31 | 0.00 | 0.00 | 4.535 |
| 2 | 6 | 126.95 | 80.12 | 46.83 | 0.00 | 0.00 | 4.311 |
| 3 | 1 | 0.00 | 181.12 | 0.00 | 34.60 | 0.00 | |
| 3 | 2 | 0.00 | 159.58 | 0.00 | 47.26 | 104.77 | |
| 3 | 3 | 0.00 | 142.63 | 0.00 | 57.22 | 118.23 | 3.112 |
| 3 | 4 | 0.00 | 128.93 | 0.00 | 65.27 | 128.56 | 2.991 |
| 3 | 5 | 0.00 | 117.63 | 0.00 | 71.91 | 136.73 | 2.798 |
| 3 | 6 | 0.00 | 108.15 | 0.00 | 77.48 | 143.35 | 3.271 |
| 4 | 1 | 0.00 | 104.33 | 0.00 | 79.73 | 148.83 | 3.258 |
| 4 | 2 | 0.00 | 86.08 | 0.00 | 90.45 | 156.12 | 3.062 |
| 4 | 3 | 0.00 | 73.27 | 0.00 | 97.98 | 160.76 | 2.176 |
| 4 | 4 | 0.00 | 63.77 | 0.00 | 103.56 | 164.62 | 2.228 |
| 4 | 5 | 0.00 | 56.46 | 0.00 | 107.86 | 167.88 | 2.407 |
| 4 | 6 | 0.00 | 0.00 | 0.00 | 0.00 | 170.67 | 5.224 |
| 4 | 6 | 0.00 | 0.00 | 0.00 | 0.00 | 0.00 | |

TABLE 6

Library: Plate3 (ID: 100279) Unit: mg

| Row | Col | water | B-SM-20-TeA | X—Cl-3 | X—Cl-2 | Phosphate binding (mmol/gr) |
|---|---|---|---|---|---|---|
| 1 | 1 | 123.95 | 108.47 | 15.49 | 0.00 | |
| 1 | 2 | 124.34 | 104.88 | 19.47 | 0.00 | |
| 1 | 3 | 124.70 | 101.51 | 23.19 | 0.00 | |
| 1 | 4 | 125.04 | 98.36 | 26.68 | 0.00 | |

TABLE 6-continued

Library: Plate3 (ID: 100279) Unit: mg

| Row | Col | water | B-SM-20-TeA | X—Cl-3 | X—Cl-2 | Phosphate binding (mmol/gr) |
|---|---|---|---|---|---|---|
| 1 | 5 | 125.36 | 95.40 | 29.97 | 0.00 | 3.958 |
| 1 | 6 | 125.66 | 92.61 | 33.06 | 0.00 | 4.309 |
| 2 | 1 | 126.13 | 88.30 | 37.82 | 0.00 | 4.417 |
| 2 | 2 | 126.47 | 85.14 | 41.33 | 0.00 | 4.424 |
| 2 | 3 | 126.78 | 82.19 | 44.59 | 0.00 | 4.392 |
| 2 | 4 | 127.08 | 79.44 | 47.64 | 0.00 | 4.407 |
| 2 | 5 | 127.36 | 76.87 | 50.49 | 0.00 | 4.14 |
| 2 | 6 | 127.62 | 74.46 | 53.16 | 0.00 | 4.314 |
| 3 | 1 | 0.00 | 118.41 | 0.00 | 26.19 | |
| 3 | 2 | 0.00 | 102.78 | 0.00 | 29.56 | |
| 3 | 3 | 0.00 | 90.80 | 0.00 | 32.14 | |
| 3 | 4 | 0.00 | 81.32 | 0.00 | 34.18 | |
| 3 | 5 | 0.00 | 73.64 | 0.00 | 35.84 | |
| 3 | 6 | 0.00 | 67.28 | 0.00 | 37.21 | 2.237 |
| 4 | 1 | 0.00 | 58.81 | 0.00 | 39.03 | 2.403 |
| 4 | 2 | 0.00 | 53.43 | 0.00 | 40.19 | 2.704 |
| 4 | 3 | 0.00 | 48.96 | 0.00 | 41.15 | 2.614 |
| 4 | 4 | 0.00 | 45.17 | 0.00 | 41.97 | 1.714 |
| 4 | 5 | 0.00 | 41.93 | 0.00 | 42.67 | 2.294 |
| 4 | 6 | 0.00 | 0.00 | 0.00 | 0.00 | 5.295 |

TABLE 7

Library: Plate1 (ID: 100353) Unit: mg

| Row | Col | B-SM-20-TeA | B-SM-22-DA | X—Cl-3 | NaOH | Phosphate binding (mmol/gr) |
|---|---|---|---|---|---|---|
| 1 | 1 | 142.77 | 11.14 | 33.97 | 24.05 | |
| 1 | 2 | 117.71 | 9.19 | 44.82 | 31.73 | |
| 1 | 3 | 100.13 | 7.82 | 52.42 | 37.12 | 5.838 |
| 1 | 4 | 87.12 | 6.80 | 58.05 | 41.10 | 5.38 |
| 1 | 5 | 77.10 | 6.02 | 62.39 | 44.17 | 5.549 |
| 1 | 6 | 69.15 | 5.40 | 65.83 | 46.61 | 5.826 |
| 2 | 1 | 64.71 | 5.05 | 67.75 | 47.97 | 5.452 |
| 2 | 2 | 57.99 | 4.53 | 70.66 | 50.03 | 3.358 |
| 2 | 3 | 52.54 | 4.10 | 73.01 | 51.70 | 3.45 |
| 2 | 4 | 48.02 | 3.75 | 74.97 | 53.08 | 4.27 |
| 2 | 5 | 44.22 | 3.45 | 76.61 | 54.24 | 3.469 |
| 2 | 6 | 40.98 | 3.20 | 78.02 | 55.24 | 4.058 |
| 3 | 1 | 111.71 | 26.16 | 39.87 | 28.23 | |
| 3 | 2 | 89.37 | 20.93 | 51.04 | 36.14 | |
| 3 | 3 | 74.48 | 17.44 | 58.49 | 41.41 | 5.154 |
| 3 | 4 | 63.85 | 14.95 | 63.81 | 45.18 | 5.784 |
| 3 | 5 | 55.87 | 13.08 | 67.80 | 48.01 | 5.596 |
| 3 | 6 | 49.66 | 11.63 | 70.91 | 50.20 | 5.287 |
| 4 | 1 | 46.24 | 10.83 | 72.62 | 51.42 | 5.261 |
| 4 | 2 | 41.13 | 9.63 | 75.17 | 53.23 | 4.743 |
| 4 | 3 | 37.04 | 8.67 | 77.22 | 54.67 | 4.076 |
| 4 | 4 | 33.69 | 7.89 | 78.90 | 55.86 | 3.924 |
| 4 | 5 | 30.90 | 7.24 | 80.29 | 56.85 | 2.896 |
| 4 | 6 | 0.00 | 0.00 | 0.00 | 0.00 | 5.287 |

TABLE 8

Library: Plate1 (ID: 100384) Unit: mg

| Row | Col | X—Cl-3 | B-SM-22-DA | water | NaOH | Phosphate binding (mmol/gr) |
|---|---|---|---|---|---|---|
| 1 | 1 | 643.88 | 422.44 | 1752.36 | 227.94 | |
| 1 | 2 | 692.40 | 378.56 | 1743.80 | 245.12 | 4.362 |
| 1 | 3 | 731.79 | 342.94 | 1736.85 | 259.06 | 4.09 |
| 1 | 4 | 764.40 | 313.44 | 1731.10 | 270.61 | 3.198 |
| 1 | 5 | 791.85 | 288.62 | 1726.26 | 280.33 | 2.951 |
| 1 | 6 | 815.27 | 267.44 | 1722.12 | 288.62 | 2.005 |
| 2 | 1 | 643.88 | 422.44 | 1752.36 | 227.94 | |

TABLE 8-continued

Library: Plate1 (ID: 100384) Unit: mg

| Row | Col | X—Cl-3 | B-SM-22-DA | water | NaOH | Phosphate binding (mmol/gr) |
|---|---|---|---|---|---|---|
| 2 | 2 | 692.40 | 378.56 | 1743.80 | 245.12 | |
| 2 | 3 | 731.79 | 342.94 | 1736.85 | 259.06 | |
| 2 | 4 | 764.40 | 313.44 | 1731.10 | 270.61 | 4.794 |
| 2 | 5 | 791.85 | 288.62 | 1726.26 | 280.33 | |
| 2 | 6 | 815.27 | 267.44 | 1722.12 | 288.62 | 4.332 |
| 3 | 1 | 643.88 | 422.44 | 1752.36 | 227.94 | |
| 3 | 2 | 692.40 | 378.56 | 1743.80 | 245.12 | |

TABLE 8-continued

| Library: Plate1 (ID: 100384) Unit: mg | | | | | | |
|---|---|---|---|---|---|---|
| Row | Col | X—Cl-3 | B-SM-22-DA | water | NaOH | Phosphate binding (mmol/gr) |
| 3 | 3 | 731.79 | 342.94 | 1736.85 | 259.06 | |
| 3 | 4 | 764.40 | 313.44 | 1731.10 | 270.61 | 4.511 |
| 3 | 5 | 791.85 | 288.62 | 1726.26 | 280.33 | 5.086 |
| 3 | 6 | 815.27 | 267.44 | 1722.12 | 288.62 | 4.61 |
| 4 | 1 | 643.88 | 422.44 | 1752.36 | 227.94 | |
| 4 | 2 | 692.40 | 378.56 | 1743.80 | 245.12 | |
| 4 | 3 | 731.79 | 342.94 | 1736.85 | 259.06 | |
| 4 | 4 | 764.40 | 313.44 | 1731.10 | 270.61 | |
| 4 | 5 | 791.85 | 286.62 | 1726.26 | 280.33 | 4.816 |
| 4 | 6 | 0.00 | 0.00 | 0.00 | 0.00 | 5.17 |

Example 2

Synthesis of 1,3-Diaminopropane/Epichlorohydrin Crosslinked Beads Formed in a Suspension Process A 3-liter reaction vessel was used, comprising a three necked round bottom flask with four side baffles. The reaction flask was equipped with an oil heating bath, cold-water reflux condenser, and mechanical stirrer with a 3 inch propeller. To this reaction vessel was introduced a solution of 1,3-diaminopropane (90.2 g, 1.21 mole) dissolved in 90.2 g of water, surfactant (branched dodecylbenzene sulfonic acid sodium salt, 6.4 g dissolved in 100 g of water) and 1 Kg of toluene. This initial charge was agitated to 600 rpm for 2 minutes and then lowered to 300 rpm for 10 minutes before the epichlorohydrin was added. The 300 rpm speed was maintained through out the remainder of the experiment. The solution was heated to 80° C. and also maintained at this temperature through out the experiment.

In a separate vessel, a 40 mass % solution of epichlorohydrin in toluene was prepared. Using a syringe pump, 1.2 equivalents of epichlorohydrin (134.7 g, (1.45 mole)) were added to the initial charge reaction vessel over a 3 hour period. The reaction was continued for an additional 2 hours before adding 0.75 equivalents of sodium hydroxide (36.5 g (0.91 mole)) in a 40 weight % solution. The sodium hydroxide solution was added to the reaction via a syringe pump over a 2.5 hour period. The reaction was maintained at 80° C. for a further 8 hours.

After this time, beads that formed were purified by removing the toluene, washing with 1000 ml of acetone, followed by methanol, a 20% solution of NaOH (to remove the surfactant), and then twice more with deionized water. The beads were freeze dried for 3 days to give a fine white powder weighing at 160 g (92% yield) and having a mean diameter of 93 μm.

Example 3

Synthesis of 1,3-Diaminopropane/1,3-Dichloropropane Crosslinked Polymer

Using water as solvent, 1000 mg of B-SM-22-DA was mixed with 1524 mg of X—Cl-3 and 2524 mg of water in a 20 mL scintillation vial. The reaction was subjected to magnetic stirring and maintained at a temperature of 80° C. overnight, followed by a temperature of 90° C. for two additional hours. A 34 wt. % of reaction mixture (1716 mg) was purified by 3 washing in water/centrifugation steps and gave 144.7 mg of powder of the polymer of the present example.

Example 4

Synthesis of 1,3-Diaminopropane/1,3-Dichloropropane Crosslinked Polymer

Using water as a solvent, 2000 mg of B-SM-22-DA was mixed with 3048 mg of X—Cl-3 and 5048 mg of water in a 20 mL scintillation vial. The reaction was subjected to magnetic stirring and maintained at a temperature of 80° C. overnight.

3597 mg of NaOH solution at 30 wt. % in water was added after 3 hours of reaction to scavenge the acid formed during the reaction as the crosslinker used was an alkylhalide. A 20.3 wt. % of reaction mixture (2773.5 mg) was purified by 3 washing in water/centrifugation steps and gave 591.3 mg of powder of the polymer of the present example.

Example 5

Synthesis of Crosslinked Beads Prepared with 1,3-Diaminopropane/1,3-dichloropropane Using a Prepolymer Approach

Preparation of Pre-Polymer

The reaction vessel used was a 250 mL, two necked round bottom flask, equipped with a cold-water reflux condenser, magnetic stirrer, and run over an argon atmosphere. To this reaction vessel is introduced a solution of 1,3-diaminopropane (31.15 g, 0.42 mole) dissolved in 30.15 g of water. This initial charge is agitated to 300 rpm. The solution was heated to 80° C. and maintained at this temperature through out the experiment. Using a syringe pump, 1 equivalent (47.47 g, 40.0 mL, 0.42 mol) of 1,3 dichloropropane (Aldrich 99%) was added over a 2-hour period. The reaction was continued for an additional 2 hours before adding 10 mole % (with respect to 1,3-diaminopropane) of sodium hydroxide (1.68 g (0.042 mole) of NaOH and made up to a 40 weight % solution of water). The sodium hydroxide solution was added to the reaction via pipette over a 2 minute period. The reaction was maintained at 80° C. for a further 4 hours. The solution at 80° C. is viscous and upon cooling to 25° C. becomes a solid plug that is readily soluble in water.

Purification

To the solid plug water is added, washing with 200 ml of water and 200 mL of MeOH. This is then added to a 1 L beaker that contains a 50/50 solution of MeOH/Isopropyl alcohol. The white polymer precipitates. After placing the suspension into a centrifuge, the supernatant liquid is removed. This process is repeated using isopropyl alcohol a further 2 times. The white precipitate is then dried under reduced pressure at room temperature to remove the isopropyl alcohol. Weight of polymer isolated: Mn (GPC relative to polyethylenimine standard) ~600.

Synthesis of Crosslinked Particles

The white pre-polymer (8.7 g) was placed into a flask with 1.3 g of branched dodecylbenzene sulfonic acid sodium salt (30 wgt % solution in water) and 34.8 g of toluene. This gave a 20 weight % solution of polymer suspended in toluene. The polymer was ground to micron sized particles with a mechanical grinder (Brand: IKA. Model: Ultra-Turax T8). 2.2 g of the resulting suspension was loaded into a 10 mL reaction flask equipped with a heater, a mechanical stirrer, and a syringe pump. The reaction flask was charged with an additional 3779 mg of toluene. The flask was heated to 80° C. and the stirrer was turned on (500 RPM). After 3 hours of stirring at this temperature, 112.2 mg (0.0012 mole) of epichlorohydrin was added over a 1.5-hour period. The reaction was allowed to proceed a further 2 hours before the addition of 224.4 mg (0.0056 mol) of sodium hydroxide (in a 40 weight % solution of water), which was delivered over a 2 hour period. The reaction was allowed to cool to room temperature and the stirring was stopped. The beads were purified by removing the toluene, washing with methanol, and then a 20% solution of NaOH (to remove the surfactant) and twice more with deionized water. The beads were freeze dried for 3 days to give a fine white powder. The binding capacity measured in a non interfering buffer was 3.85 mmol/gr.

Example 6

Synthesis of Micron Sized, Crosslinked Beads with N,N'(tetra-3-aminopropyl) 1,4 diaminobutane/epichlorohydrin Via Inverse Suspension Materials:

| | |
|---|---|
| Name | N,N,N',N'-Tetrakis(3-aminopropyl)-1,4-butanediamine |
| Molecular Formula | 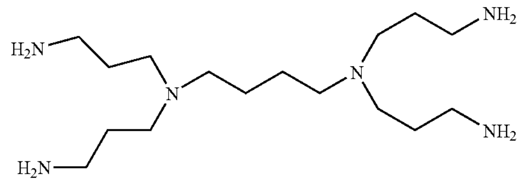 $C_{16}H_{40}N_6$ |
| Molecular Weight | 316.53 |
| CAS Number | 120239-63-6 |
| Name | Epichlorohydrin; 1-Chloro-2,3-epoxypropane (±)-2-(Chloromethyl)oxirane |
| Molecular Formula | $C_3H_5ClO$ 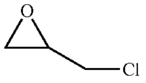 |
| Molecular Weight | 92.52 |
| CAS Number | 106-89-8 |
| Purity | >99% |
| Name | Toluene |
| Molecular Formula | $C_7H_8$ |
| Molecular Weight | 92.14 |
| CAS Number | 108-88-3 |
| Name | Dodecylbenzenesulfonic acid sodium salt Branched 30% in water. |
| Molecular Formula | 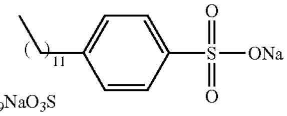 $C_{18}H_{29}NaO_3S$ |
| Molecular Weight | 348.48 |
| CAS Number | 25155-30-0 |

Method

The following stock solution was prepared: 2 molar equivalents of concentrated HCl was added to 1 molar equivalent of N,N,N',N'-Tetrakis(3-aminopropyl)-1,4-butanediamine over a 2 hour period. Water and surfactant (branched dodecylbenzene sulfonic acid sodium salt, 30 weight % in water) was then added to the solution such that the resulting solution achieved the following weight % composition: N,N,N',N'-Tetrakis(3-aminopropyl)-1,4-butanediamine 41.8 weight %, HCl 9.4 weight %, water 41.1 weight %, surfactant (30 weight % in water) 7.7 weight %.

The following is a selected example of a reaction that was conducted in a 3 liter, three necked round bottom flask with four side baffles, equipped with an oil heating bath, a thermometer to measure the internal reaction temperature, a cold-water reflux condenser and mechanical stirrer with a 1 inch propeller. To this reaction vessel is introduced 362.3 g of the prepared stock solution and 1086 g of toluene. This initial charge is agitated to 600 rpm for 2 minutes and then lowered to 240 rpm for 10 minutes before the first addition of epichlorohydrin. This speed is maintained through out the experiment. The solution was heated to 80° C. and maintained at this temperature through out the experiment. The reaction is purged for 20 minutes with nitrogen before the addition of epichlorohydrin and as the reaction proceeds, a blanket of nitrogen is maintained.

Into a separate vessel, a 40 mass % stock solution of epichlorohydrin in toluene was prepared. Using a syringe pump, 2.5 molar equivalents of epichlorohydrin, in the stock solution was added over a 90 minute period. Six hours after adding the epichlorohydrin, the reaction was finished by the removal of heat and is allowed to cool with a nitrogen purge.

The beads were purified by removing the toluene, washing with methanol and then a 20% solution of NaOH (to remove the surfactant) till a pH of 11 was achieved. The beads were washed with methanol and then allowed to drain. The beads were then placed into a soxhlet apparatus with a nitrogen purge and washed with deionized water for 12 hours. The beads were then placed into a pan, frozen and freeze dried (using a lyophilizer) for 3 days to give a fine white powder.

The methods described in the Examples can be used, with or without modifications, to synthesize crosslinked polymers with other amines, such as the amines related to Formulas V''', VII, VIII, and IX.

Example 7

Binding Capacity in a Digestion Model

This procedure was designed to mimic the conditions of use of a phosphate binding polymer in a GI tract and measure the binding characteristics of the polymer for phosphate (target solute) in the presence of other metabolites (competing solutes). A liquid meal was prepared and the polymers of each of Examples 2, 3, or 4 were added to the meal composition and the meal was artificially digested in the presence of pepsin and pancreatic juice. The sequence of addition of enzymes and the pH profile were controlled so that the digestion process was simulated down to the jejunum level. An aliquot of the digested meal mimic was centrifuged and the supernatant assayed for phosphate. The phosphate binding assay was like the one described above with non-interfering buffer, except that liquid of the meal digest mimic was used. The binding capacity in the meal digest was calculated as indicated above and results are reported in Table 9 below.

TABLE 9

| | Phosphate binding in a non interfering buffer | | | Phosphate binding in a meal digest | | |
|---|---|---|---|---|---|---|
| Example | $C_{start}$ (mM) | $C_{eq}$ (mM) | Capacity (mmol/gr) | $C_{start}$ (mM) | $C_{eq}$ (mM) | Capacity (mmol/gr) |
| 2 | 20.1 | 10.56 | 3.81 | 8.01 | 5.31 | 1.08 |
| 3 | 20.1 | 12.27 | 3.13 | 8.01 | 5.83 | 0.74 |
| 4 | 20.1 | 9.32 | 4.31 | 8.01 | 3.87 | 1.66 |

Example 8

Coating of Micron Sized Polyamine Bead with a Water Soluble Shell

The reactions were conducted in a 24-well polymerization reactor that used 4 mL vials+stir bars. A commercially available liquid handling robot driven by Symyx Technologies software was used to deliver the reagents to the vials. A typical reaction procedure is as follows: into each 4 mL vial is placed 0.3 g of the polyamine bead material of Example 6. Water is added to the beads. The stirrers are turned on. A 20 weight % solution of Polyacrylic acid in water was prepared. The desired amount of poly acrylic acid was added using the dispensing robot to the 4 mL vials which were at room temperature. The reactions were conducted such that the polyamine type beads represent 12 weight % of the water and Polyacrylic acid added. After addition of the polyacrylic acid to the water bead solution, the reaction plate was heated to 85° C. for 12 hours. The beads in the 4 mL vials were then transferred to an 8 mL test tube and washed with ~6 mL deionized water to remove excess polyacrylic acid. The water wash procedure was repeated another 3 times. The beads were freeze dried for 3 days to give a fine white powder. The samples were characterized for swelling, phosphate binding and citrate binding in a synthetic GI mimic as described in Example 7.

The results are summarized in Tables 10-13.

TABLE 10

| Label | Name | CAS # | MW (g/mol) |
|---|---|---|---|
| Shell-A-4 | Poly(acrylic acid co maleic acid) | | 3000 |
| Shell-A-5 | PolyAcrylic Acid | 323667 | 5,000 |
| Shell-A-6 | PolyAcrylic Acid | 323667 | 50,000 |
| Shell-A-7 | PolyAcrylic Acid | 323667 | 90,000 |
| Shell-A-8 | PolyAcrylic Acid | 323667 | 250,000 |

TABLE 11

First exploration of Poly(acrylic acid-co maleic acid) + Poly-amine bead.

| Sample No. | Polyamine bead ID | Shell ID | Shell wt % | Phosphate BC (mmol/g) | Citrate BC (mmol/g) | Swelling (g H2O/g Gel) |
|---|---|---|---|---|---|---|
| 1.00 | FR-26-52-1 | Shell-A-4 | 0.05 | 2.03 | 0.05 | 2.63 |
| 2.00 | FR-26-52-1 | Shell-A-4 | 0.13 | 1.99 | 0.05 | 2.54 |
| 3.00 | FR-26-52-1 | Shell-A-4 | 0.21 | 1.99 | 0.05 | 2.79 |
| 4.00 | FR-26-52-1 | Shell-A-4 | 0.29 | 1.95 | 0.07 | 2.47 |
| 5.00 | FR-26-52-1 | Shell-A-4 | 0.37 | 1.91 | 0.05 | 2.43 |
| 6.00 | FR-26-52-1 | Shell-A-4 | 0.45 | 1.83 | 0.10 | 2.39 |
| 7.00 | FR-26-52-1 | Shell-A-4 | 0.50 | 1.84 | 0.05 | 2.97 |
| 8.00 | FR-26-52-1 | Shell-A-4 | 0.65 | 1.84 | 0.05 | 2.74 |
| 9.00 | FR-26-52-1 | Shell-A-4 | 0.85 | 1.80 | 0.03 | 2.42 |
| 10.00 | FR-26-52-1 | Shell-A-4 | 1.00 | 1.74 | 0.04 | 2.41 |
| 11.00 | FR-26-52-1 | Shell-A-4 | 0.00 | 1.59 | 0.26 | 2.17 |

TABLE 12

Second exploration of Poly(acrylic acid-co maleic acid) + Poly(amine) bead.

| Sample No. | Polyamine bead ID | Shell ID | Shell wt % | Phosphate BC (mmol/g) | Citrate BC (mmol/g) | Swelling (g H2O/g Gel) |
|---|---|---|---|---|---|---|
| 1 | FR-26-52-1 | Shell-A-4 | 0.00 | 1.55 | 0.38 | 2.20 |
| 2 | FR-26-52-1 | Shell-A-4 | 0.03 | 2.00 | 0.04 | 2.45 |
| 3 | FR-26-52-1 | Shell-A-4 | 0.06 | 2.01 | 0.04 | 2.50 |
| 4 | FR-26-52-1 | Shell-A-4 | 0.09 | 1.98 | 0.06 | 2.46 |
| 5 | FR-26-52-1 | Shell-A-4 | 0.12 | 1.98 | 0.02 | 2.60 |
| 6 | FR-26-52-1 | Shell-A-4 | 0.15 | 1.93 | 0.09 | 2.47 |
| 7 | FR-26-52-1 | Shell-A-4 | 0.20 | 1.95 | 0.05 | 2.35 |
| 8 | FR-26-52-1 | Shell-A-4 | 0.30 | 1.93 | 0.05 | 2.49 |
| 9 | FR-26-52-1 | Shell-A-4 | 0.40 | 1.90 | 0.04 | 2.50 |
| 10 | FR-26-52-1 | Shell-A-4 | 0.50 | 1.89 | 0.04 | 2.29 |

TABLE 13

Exploration of Poly(acrylic acid) of different Molecular weights + Poly-amine bead

| Sample No. | Polyamine bead ID | Shell ID | Shell wt % | Phosphate BC (mmol/g) | Citrate BC (mmol/g) | Swelling (g H2O/g Gel) |
|---|---|---|---|---|---|---|
| 1 | FR-26-52-1 | Shell-A-5 | 0.10 | 1.91 | 0.37 | 2.49 |
| 2 | FR-26-52-1 | Shell-A-5 | 0.28 | 1.84 | 0.37 | 2.54 |
| 3 | FR-26-52-1 | Shell-A-5 | 0.46 | 1.92 | 0.35 | 2.56 |
| 4 | FR-26-52-1 | Shell-A-5 | 0.64 | 1.85 | 0.37 | 2.52 |
| 5 | FR-26-52-1 | Shell-A-5 | 0.82 | 1.84 | 0.37 | 2.49 |
| 6 | FR-26-52-1 | Shell-A-5 | 1.00 | 1.80 | 0.39 | 2.56 |
| 7 | FR-26-52-1 | Shell-A-6 | 0.10 | 1.89 | 0.30 | 2.49 |
| 8 | FR-26-52-1 | Shell-A-6 | 0.28 | 1.87 | 0.25 | 2.41 |
| 9 | FR-26-52-1 | Shell-A-6 | 0.46 | 1.92 | 0.21 | 2.44 |
| 10 | FR-26-52-1 | Shell-A-6 | 0.64 | 1.88 | 0.17 | 2.54 |
| 11 | FR-26-52-1 | Shell-A-6 | 0.82 | 1.88 | 0.20 | 2.42 |
| 12 | FR-26-52-1 | Shell-A-6 | 1.00 | 1.87 | 0.22 | 2.42 |

TABLE 13-continued

| Exploration of Poly(acrylic acid) of different Molecular weights + Poly-amine bead | | | | | | |
|---|---|---|---|---|---|---|
| Sample No. | Polyamine bead ID | Shell ID | Shell wt % | Phosphate BC (mmol/g) | Citrate BC (mmol/g) | Swelling (g H2O/g Gel) |
| 13 | FR-26-52-1 | Shell-A-7 | 0.10 | 1.93 | 0.19 | 2.52 |
| 14 | FR-26-52-1 | Shell-A-7 | 0.28 | 1.93 | 0.17 | 2.47 |
| 15 | FR-26-52-1 | Shell-A-7 | 0.46 | 1.91 | 0.15 | 2.45 |
| 16 | FR-26-52-1 | Shell-A-7 | 0.64 | 1.88 | 0.13 | 2.47 |
| 17 | FR-26-52-1 | Shell-A-7 | 0.82 | 1.87 | 0.13 | 2.39 |
| 18 | FR-26-52-1 | Shell-A-7 | 1.00 | 1.90 | 0.16 | 2.43 |
| 19 | FR-26-52-1 | Shell-A-8 | 0.10 | 1.93 | 0.26 | 2.39 |
| 20 | FR-26-52-1 | Shell-A-8 | 0.32 | 1.92 | 0.18 | 2.53 |
| 21 | FR-26-52-1 | Shell-A-8 | 0.54 | 1.89 | 0.17 | 2.54 |
| 22 | FR-26-52-1 | Shell-A-8 | 0.76 | 1.85 | 0.15 | 2.43 |
| 23 | FR-26-52-1 | | 0.00 | 1.53 | 0.40 | 2.33 |

These examples show a significant increase in overall binding when a polyanionic polymer is deposited as a shell material over the controls (i.e. no shell present).

Example 9

Binding Capacity in Ex-Vivo Aspirates

Using a tube placed in the lumen of the small intestine, healthy patients are given a meal of the same composition as the one prepared for the digestion mimic in Example 6 and aliquots of chyme are then sampled.

Subjects are intubated with a double lumen polyvinyl tube with a mercury-weighted bag attached to the end of the tube to facilitate movement of the tube into the small intestine. Using fluoroscopy to direct placement, one aspiration aperture of the double lumen tube is located in the stomach, and the other aperture is at the Ligament of Treitz (in the upper jejunum).

After correct tube placement, 550 mL of the liquefied test meal (supplemented with a marker, polyethylene glycol (PEG)-2 g/550 mL) is infused into the stomach through the gastric aperture at a rate of 22 mL per minute. It requires approximately 25 minutes for the entire meal to reach the stomach, simulating the duration of time required to eat normal meals.

Jejunal chyme is aspirated from the tube whose lumen is located at the Ligament of Treitz. This fluid is collected continuously during 30 minute intervals for a two and a half hour period. This results in 5 specimens that are mixed, measured for volume, and lyophilized.

A phosphate binding assay can be carried out on the ex-vivo aspirates. The phosphate binding procedure can be like the one described above with non-interfering buffer, except that the ex-vivo aspirate liquid is used (after reconstitution of the freeze-dried material in the proper amount of de-ionized water). The phosphate binding capacities in the ex-vivo aspirate can be calculated in the same way and are expected to be similar to those reported with the meal mimic experiments.

What is claimed is:

1. A crosslinked amine polymer comprising repeat units derived from polymerization of an amine of formula VIII (VIII)

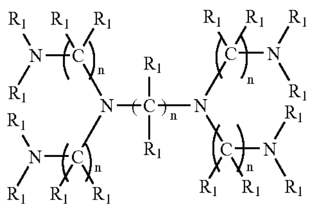

and a crosslinking agent, wherein each n, independently, is equal to or greater than 3; and each $R_1$, independently, is H or optionally substituted alkyl or aryl or is linked to a neighboring $R_1$ to form an optionally substituted alicyclic, aromatic, or heterocyclic group, with the proviso that said amine is not an amine of formula V'

(V')

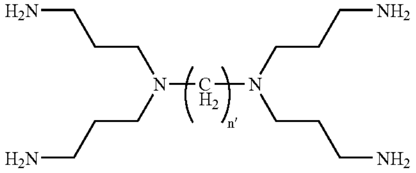

wherein n' is 3, 4, or 5 and the amine is not an amine having the following formula

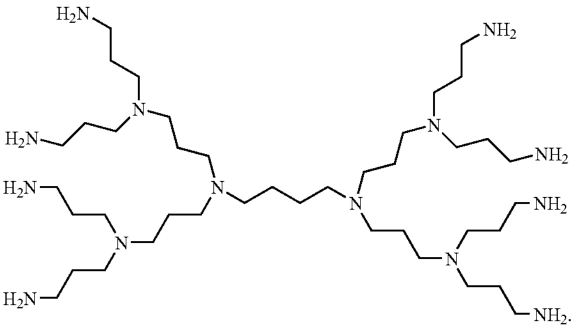

2. The polymer of claim 1 comprising repeat units derived from polymerization of the amine of formula X (X)

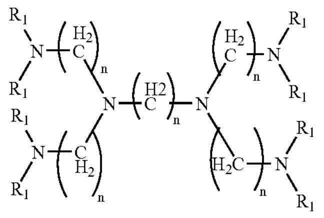

and the crosslinking agent, wherein each n and $R_1$ are as defined in claim 1.

3. The polymer of claim 1 comprising repeat units derived from polymerization of the amine of formula IX (IX)

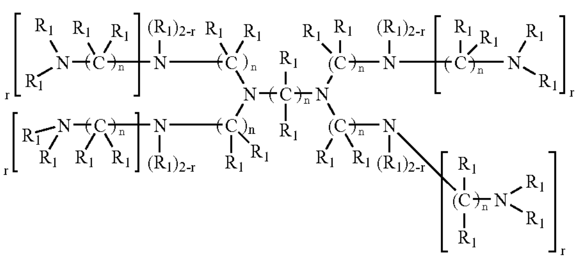

and a crosslinking agent, wherein r is 0, 1, or 2 and each n and $R_1$ are as defined in claim 1.

4. The polymer of claim 1 wherein each n, independently, is 3 to 10.

5. The polymer of claim 1 wherein each n, independently, is 6 to 10.

6. The polymer of claim 1 wherein the crosslinking agent is a compound having at least two functional groups, each functional group being selected from halogen, carbonyl, epoxy, ester, acid anhydride, acid halide, isocyanate, vinyl, and chloroformate.

7. The polymer of claim 1 wherein said crosslinking agent is 1,3-dichloropropane or epichlorohydrin.

8. The polymer of claim 1 comprising repeat units derived from polymerization of an amine of the formula V'''

(V''')

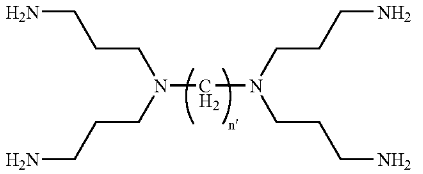

and a crosslinking agent, wherein n' is equal to or greater than 6.

9. The polymer of claim 8 wherein n' is 6-20.

10. The polymer of claim 8 wherein n' is 6-10.

11. The polymer of claim 8 wherein n' is 6-8.

12. A crosslinked amine polymer comprising repeat units derived from polymerization of an amine of formula VIII (VIII)

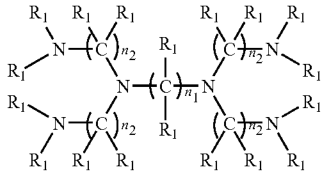

and a crosslinking agent, wherein $n_1$ is 6 to 10, each $n_2$, independently, is 3 to 10; and each $R_1$, independently, is H or optionally substituted alkyl or aryl or is linked to a neighboring $R_1$ to form an optionally substituted alicyclic, aromatic, or heterocyclic group.

13. The polymer of claim 12 comprising repeat units derived from polymerization of an amine of formula X (X)

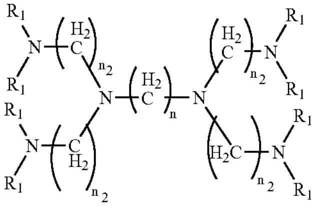

and a crosslinking agent, wherein each $n_1$, $n_2$, and $R_1$ are as defined in claim 12.

14. The polymer of claim 12 comprising repeat units derived from polymerization of an amine of formula IX (IX)

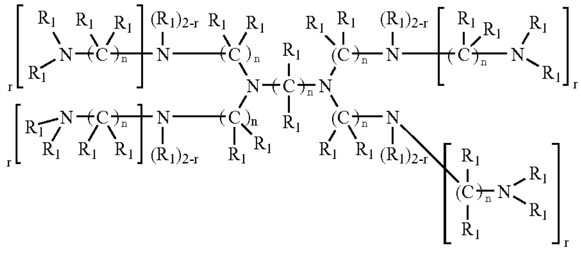

and a crosslinking agent, wherein each r, $n_1$, $n_2$, and $R_1$ are as defined in claim 12.

15. The polymer of claim 12 wherein each $n_2$, independently, is 6 to 10.

16. The polymer of claim 12 wherein the crosslinking agent is a compound having at least two functional groups, each functional group being selected from halogen, carbonyl, epoxy, ester, acid anhydride, acid halide, isocyanate, vinyl, and chloroformate.

17. The polymer of claim 12 wherein said crosslinking agent is 1,3-dichloropropane or epichlorohydrin.

18. A pharmaceutical composition comprising the polymer of claim 1 and a pharmaceutically acceptable carrier.

19. A pharmaceutical composition comprising the polymer of claim 12 and a pharmaceutically acceptable carrier.

20. The pharmaceutical composition of claim 18 wherein the crosslinked amine polymer has a phosphate binding capacity in a non-interfering buffer ranging from about 0.5 mmol/g to about 10 mmol/g.

21. The pharmaceutical composition of claim 19 wherein the crosslinked amine polymer has a phosphate binding capacity in a non-interfering buffer ranging from about 0.5 mmol/g to about 10 mmol/g.

22. A composition comprising core-shell particles, said core-shell particles comprising a polymeric core microencapsulated in a polymeric shell, the polymeric core comprising the polymer of claim 1.

23. A method of removing phosphate from an animal comprising administering an effective amount of a crosslinked amine polymer comprising repeat units derived from polymerization of an amine of formula VII (VII)

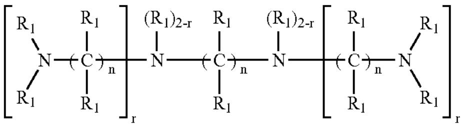

and a crosslinking agent, wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group, with the proviso that said amine is not an amine of formula V'

(V')

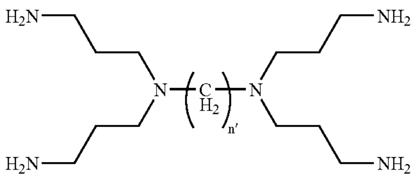

wherein n' is 3, 4, or 5.

24. The method of claim 23 with the proviso that said amine is not a compound of formula V (V)

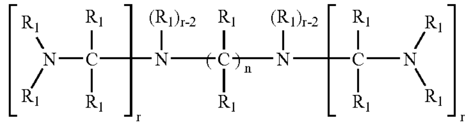

wherein each n, r and $R_1$ are as defined in claim 23.

25. The method of claim 23 with the proviso that said amine is not a compound of formula V"

(V")

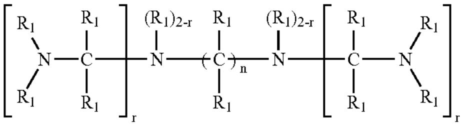

wherein each n, r, and $R_1$ are as defined in claim 23.

26. The method of claim 23 where each n, independently, is 3 to 10.

27. The method of claim 23 wherein each n, independently, is 6 to 10.

28. A method of removing phosphate from an animal comprising administering an effective amount of the polymer of claim 1.

29. A method of removing phosphate from an animal comprising administering an effective amount of the polymer of claim 12.

30. The pharmaceutical composition of claim 18 wherein the composition is in a capsule form suitable for oral administration.

31. The pharmaceutical composition of claim 19 wherein the composition is in a capsule form suitable for oral administration.

* * * * *

UNITED STATES PATENT AND TRADEMARK OFFICE

CERTIFICATE OF CORRECTION

PATENT NO. : 7,767,768 B2
APPLICATION NO. : 11/577194
DATED : August 3, 2010
INVENTOR(S) : Chang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 311 days.

Signed and Sealed this
Eighth Day of March, 2011

David J. Kappos
*Director of the United States Patent and Trademark Office*